(12) United States Patent
He et al.

(10) Patent No.: US 10,434,511 B2
(45) Date of Patent: Oct. 8, 2019

(54) NON-INVASIVE MONITORING CANCER USING INTEGRATED MICROFLUIDIC PROFILING OF CIRCULATING MICROVESICLES

(71) Applicant: University of Kansas, Lawrence, KS (US)

(72) Inventors: Mei He, Olathe, KS (US); Yong Zeng, Olathe, KS (US); Andrew Godwin, Leawood, KS (US)

(73) Assignee: University of Kansas, Lawrence, KS (US)

( * ) Notice: Subject to any disclaimer, the term of this patent is extended or adjusted under 35 U.S.C. 154(b) by 50 days.

(21) Appl. No.: 15/125,822

(22) PCT Filed: Mar. 16, 2015

(86) PCT No.: PCT/US2015/020683
§ 371 (c)(1),
(2) Date: Sep. 13, 2016

(87) PCT Pub. No.: WO2015/139019
PCT Pub. Date: Sep. 17, 2015

(65) Prior Publication Data
US 2017/0001197 A1  Jan. 5, 2017

Related U.S. Application Data

(60) Provisional application No. 61/953,109, filed on Mar. 14, 2014, provisional application No. 62/025,151, filed on Jul. 16, 2014.

(51) Int. Cl.
*B01L 3/00* (2006.01)
*G01N 33/53* (2006.01)
(Continued)

(52) U.S. Cl.
CPC .... *B01L 3/502761* (2013.01); *G01N 33/5304* (2013.01); *G01N 33/54366* (2013.01);
(Continued)

(58) Field of Classification Search
None
See application file for complete search history.

(56) References Cited

U.S. PATENT DOCUMENTS

2005/0041525 A1   2/2005  Pugia et al.
2009/0269767 A1  10/2009  Soderlund et al.
(Continued)

FOREIGN PATENT DOCUMENTS

WO   2013/126774 A2   8/2013

OTHER PUBLICATIONS

Sivagnanam, Microfluidic Immunoassays Based on Self-Assembled Magnetic Patterns and Time-Resolved Luminescence Detection, Thesis, Ecole Polytechnique Federale De Lausanne, pp. 1-144. 2010.

*Primary Examiner* — Rebecca L Martinez
(74) *Attorney, Agent, or Firm* — Hovey Williams LLP

(57) ABSTRACT

A microfluidic exosome profiling platform integrating exosome isolation and targeted proteomic analysis is disclosed. This platform is capable of quantitative exosomal biomarker profiling directly from 30 μL plasma samples within approximately 100 minutes with markedly enhanced sensitivity and specificity. Identification of distinct subpopulation of patient-derived exosomes is demonstrated by probing surface proteins and multiparameter analyses of intravesicular biomarkers in the selected subpopulation. The expression of IGF-1R and its phosphorylation level in non-small cell lung cancer (NSCLC) patient plasma is assessed, as a non-invasive alternative to the conventional biopsy and immunohistochemistry. The microfluidic chip, which may (Continued)

be fabricated of a glass substrate and a layer of poly (dimethylsiloxane), can include a first capture chamber, a second capture chamber, a serpentine microchannel, a first microchannel, a second microchannel, a sample inlet, a buffer inlet, a bead inlet, at least a first connector channel, and a reagent inlet.

13 Claims, 17 Drawing Sheets

(51) Int. Cl.
*G01N 33/543* (2006.01)
*G01N 33/574* (2006.01)

(52) U.S. Cl.
CPC . *G01N 33/54386* (2013.01); *G01N 33/57488* (2013.01); *B01L 2200/0668* (2013.01); *B01L 2300/087* (2013.01); *B01L 2300/0816* (2013.01); *B01L 2300/0883* (2013.01); *B01L 2400/043* (2013.01); *B01L 2400/0487* (2013.01); *G01N 2333/4725* (2013.01); *G01N 2333/4745* (2013.01); *G01N 2333/70596* (2013.01); *G01N 2800/52* (2013.01)

(56) References Cited

U.S. PATENT DOCUMENTS

| | | |
|---|---|---|
| 2010/0159573 A1 | 6/2010 | Chung et al. |
| 2011/0112503 A1 | 5/2011 | Ismagilov et al. |
| 2012/0149600 A1 | 6/2012 | Lee et al. |

NON-INVASIVE MONITORING CANCER USING INTEGRATED MICROFLUIDIC PROFILING OF CIRCULATING MICROVESICLES

CROSS-REFERENCE TO RELATED APPLICATIONS

This application is the U.S. National Stage of PCT/US2015/020683, filed Mar. 16, 2015, which claims priority to the provisional patent application filed Mar. 14, 2014 and assigned U.S. App. No. 61/953,109 and the provisional patent application filed Jul. 16, 2014 and assigned U.S. App. No. 62/025,151, the disclosures of which are hereby incorporated by reference.

STATEMENT REGARDING FEDERALLY SPONSORED RESEARCH

This invention was made with government support under grant CA140323 awarded by the National Institutes of Health. The government has certain rights in the invention.

BACKGROUND OF THE DISCLOSURE

Developing non-invasive blood-based tests is extremely appealing for presymptomatic screening and early detection of cancers where obtaining tissue biopsy is highly invasive, difficult, or costly, such as lung cancer and ovarian cancer. This is particularly true for many primary tumors and most metastatic diseases. Probing circulating exosomes is an emerging paradigm for non-invasive cancer diagnosis and monitoring of treatment. Most eukaryotic cells release numerous membrane-derived vesicles into extracellular environment which are mainly composed of 10-1000 nm exosomes and microvesicles differing in their cellular origin, abundance and biogenesis. Exosomes are commonly recognized as membrane vesicles derived from the endolysosomal pathway with a size range of approximately 30-150 nm, and are abundantly found in the plasma and malignant effusions derived from cancer patients. Exosomes share certain common characteristics, including shape, size, density, and general protein composition, and mediate effects via transfer of cargo consisting of an array of proteins, selected functional cellular RNAs, and mitochondrial DNA. Despite the potential for cancer research, exosome analyses have been severely constrained by the daunting technical difficulties in isolation and molecular analysis of such nano-scale and molecularly diverse vesicles. Current isolation protocols largely rely on multiple ultracentrifugation steps, which are tedious, time-consuming (>10 h) and inefficient. Moreover, differential ultracentrifugation co-purifies several microvesicle subpopulations which are secreted by different intracellular mechanisms, and thus could potentially mask disease-related biosignature. Size exclusion methods normally do not concentrate exosomes and are prone to pressure-caused damage of vesicles and contaminations. Molecular analysis of isolated microvesicles is primarily performed using Western blot, ELISA and mass spectrometry, which require lengthy processes and large sample sizes (purified from more than 3 mL plasma or 300 mL cell culture media), limiting the progress in clinical investigation and utilities of exosomes. To date, no well-defined protocols and markers for quantitative evaluation of extracellular vesicle proteins exist.

Microfluidic technology has shown unique advantages in bioassays, such as ultrahigh throughput, single molecule/cell sensitivity and resolution, multifunctional integration, and automated operation with minimal sample consumption, to facilitate quantitative biology and medicine. Although recent advance of microfluidic technology has made an impact on many areas of biology, there is an ongoing need for microfluidic technology to accelerate exosome analysis.

SUMMARY OF THE DISCLOSURE

This disclosure, which is more fully described under the Detailed Description section below, provides in certain embodiments a "sample-in-answer-out" microfluidic exosome profiling platform which integrates exosome isolation and targeted proteomic analysis in one rapid assay. We demonstrate utility of the device and a method of using it for quantitative exosomal biomarker profiling directly from 30 µL plasma samples within ~100 min, with markedly enhanced sensitivity and specificity compared to previously available approaches.

Microfluidic chips, which can be an example of a microelectromechanical systems (MEMS) device, typically range in size from a few square millimeters to a few square centimeters. These microfluidic chips are designed to handle or manipulate small fluid volumes in order to perform biological or medical processing or testing. The fluids may be moved, mixed, or processed in a single microfluidic chip.

Microfluidic chips provide multiple advantages over conventional testing. The presently provided microfluidic chips use smaller volumes of fluids, provide faster results, are more compact and require less manual operation and lab space, increase testing throughput, reduce costs, reduce technician exposure to fluids due to the smaller amounts of fluids that are required, and can increase patient comfort due to the smaller amounts of body fluids that are required for testing. The design of these microfluidic chips can vary by applications, and each variation can use a form of microfluidics to enable fluid flow to various regions in the chip.

In this disclosure, we report for the first time an integrated microfluidic approach that enables on-chip immunoisolation and in situ analysis of exosome surface and intravesicular proteins directly from patient plasma. To this end, a cascading microfluidic circuit was designed to streamline and expedite the multi-step assay, including exosome isolation and enrichment, on-line chemical lysis and target capture, and sandwich immunoassay assisted by chemifluorescence detection.

We have employed this platform to provide a non-limiting proof of its diagnostic utility by using it to measure the expression levels of total and phosphorylated type 1 insulin growth factor receptor (IGF-1R) in non-small cell lung cancer (NSCLC) patient plasma-derived circulating exosomes, which opens a new avenue for monitoring a wide variety of biomarkers and subtle distinctions between them. For example, we are able to discriminate IGF-1R and its activation status in a non-invasive manner as a liquid biopsy. We selected IGF-1R in part because it is a pivotal therapeutic target in NSCLC and other cancers. However, current clinical assessment of IGF-1R expression primarily relies on immunohistochemistry (IHC) of tumor tissue sections. The majority of NSCLC patients present with unresectable advanced disease, thus obtaining adequate tissue biopsies prior to each therapy for diagnosis and prognosis is extremely challenging, which is invasive and substantially limits the histologic and molecular information. Overall we demonstrate the ability of this platform to detect specific circulating microvesicular markers directly from patient plasma samples, in support of using circulating microvesicles for monitoring the state of IGF-1R during therapy of NSCLC patients. Thus, it is expected that the device and methods of using it will be broadly applicable to a wide variety of markers that are, for example, detectable in exosomes or other membranous structures present in liquid biological samples.

A microfluidic chip is provided in a first embodiment. The microfluidic chip, which may be fabricated of a glass substrate, and a layer of any suitable coating, such as poly(dimethylsiloxane), includes a first capture chamber, a second capture chamber, a serpentine microchannel, a first microchannel, a second microchannel, a sample inlet, a buffer inlet, a bead inlet, at least a first connector channel, and a reagent inlet. The first capture chamber is configured to enable immunomagnetic isolation and can be configured to isolate magnetic microbeads with bound exosomes from a fluid sample. The second capture chamber is configured to enable protein analysis. In an embodiment, the first capture chamber and the second capture chamber can be approximately 4 mm in diameter and can each capture up to approximately $10^9$ 2.8 μm microbeads. The serpentine microchannel connects the first capture chamber and the second capture chamber and can have at least one surface that is hydrophilic. The first microchannel connects the first capture chamber and the serpentine microchannel. The second microchannel connects the serpentine microchannel and the second capture chamber. The sample inlet is connected to the first capture chamber. The buffer inlet is connected to the first capture chamber. The first connector channel is connected to the bead inlet and the first microchannel such that the first connector channel is connected to the first microchannel upstream of the serpentine microchannel and downstream of the first capture chamber. The first connector channel can have dimensions configured to enable magnetic microbeads to pass there through. The reagent inlet is connected to the second microchannel upstream of the second capture chamber and downstream of the serpentine microchannel.

A second connector channel can be connected to the bead inlet and the first microchannel such that the second connector channel is connected to the first microchannel upstream of the serpentine microchannel and downstream of the first capture chamber.

At least one syringe pump can be connected to one of the sample inlet, the buffer inlet, the bead inlet, or the reagent inlet. The syringe pump is configured to have picoliter resolution. For example, a four-syringe pump can be connected to the sample inlet, the buffer inlet, the bead inlet, and the reagent inlet.

A magnet can be positioned opposite of a surface of the microfluidic chip.

An outlet can be connected to the second capture chamber.

A method of diagnosis, for aiding in diagnosis, or for monitoring treatment of a subject is provided in a second embodiment. A microfluidic chip, such as that disclosed herein, is used to process a sample obtained or derived from the subject. A signal is detected from a detectably labeled antibody that is specifically bound to a marker, including but not necessarily limited to a protein marker, which was present in the sample obtained or derived from the subject. The signal from the detectably labeled antibody is generated in the second capture chamber.

The sample that is tested using the device and method of the present disclosure can be any suitable sample. In embodiments, the sample is liquid biological sample. In an embodiment, the sample is plasma. In embodiments, a liquid biological sample is used directly, without processing before introducing the sample into the device. In embodiments, the protein marker is any protein that is positively correlated with a condition, such as a disease or other disorder. In one embodiment the marker comprises a cancer marker. In embodiments, the device is suitable for testing a sample obtained or derived from any animal. In an embodiment, the animal is mammal. In an embodiment, the mammal is a human. In another embodiment, the mammal is a non-human mammal. The device and method are accordingly suitable for use in human and veterinary diagnostic approaches.

DETAILED DESCRIPTION OF THE DISCLOSURE

The present disclosure relates to a microfluidic device and methods of using it. Features and various embodiments of components of the microfluidic device of this disclosure will be apparent from the description and figures presented herein. In general, the device is used for non-invasive procedures which involve testing samples for use in monitoring the treatment of, and/or diagnosing and/or aiding in the diagnosis, of a disorder or condition that is positively correlated with the presence of one or more immunologically detectable markers that are contained within membranous structures in a biological sample.

In general, the present disclosure includes obtaining a sample and testing it as generally depicted in Table 1 presented below. In embodiments, any biological sample can be used, and can be tested directly, or can be subjected to a processing step before being tested. In embodiments, the sample is plasma obtained from a human subject. The plasma sample can be mixed with, for instance, a first antibody labeled magnetic beads reagent to obtain isolated magnetic beads with bound membranous structures, such as exosomes. The bound exosomes can be washed and subjected to a lysis buffer solution treatment to obtain a lysate. The lysate can be incubated with a second antibody labeled magnetic beads reagent to specifically capture released intravesicular proteins such that protein capture beads are provided. The protein capture beads can be exposed to detection antibodies which comprise any suitable detectable label, such as a label that can produce detectable chemifluorescence. Thus, the disclosure includes use of a microfluidic device as described further below to detect and/or quantify a complex of detectably labeled antibodies and a target protein that is present in a sample obtained and/or derived from a human subject. In embodiments, the complex is a component similar to the complex formed during a sandwich ELISA assay.

In certain embodiments, the disclosure relates to an integrated microfluidic exosome profiling platform which streamlines and expedites exosome isolation and enrichment, lysis, and targeted protein marker probing in one continuous assay. In embodiments, a cascading microfluidic circuit with at least two immunomagnetic chambers connected by channel networks are provided, allowing the specific identification of intra-vesicular markers to be correlated with its subpopulation (i.e., exosome surface markers). In one embodiment, this platform can achieve quantitative exosomal biomarker profiling directly from human plasma in a total assay time of up to not more than 100 minutes, with reduced sample consumption (30 µL), enhanced sensitivity (LOD of femtogram) and specificity, and cost-effectiveness. In embodiments, the sample size is between 1 and 30 µL, including all integers and ranges of integers there between.

Figure 4:
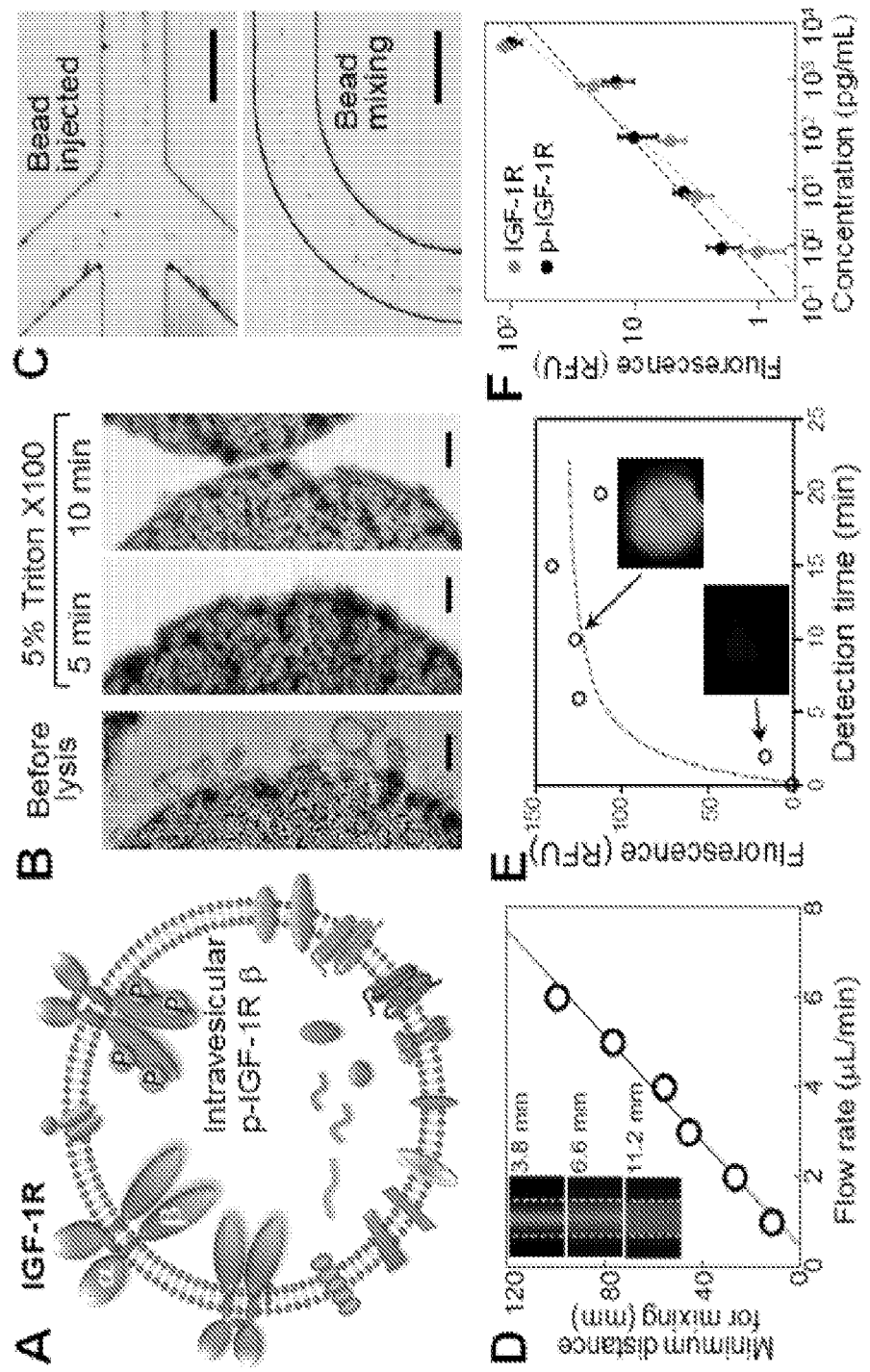
FIG. 4. Integrated microfluidic exosome analysis. (A) Schematic of transmembrane IGF-1R in exosomes. We target extravesicular IGF-1R α unit and phosphorylated β domain inside the vesicle to demonstrate surface phenotyping and intravesicular protein analysis of exosomes. (B) Chemical lysis of exosomes by Triton X-100 surfactant observed by TEM. The scale bar is 100 nm. (C) Bright field images of injection (top) and mixing (bottom) of the protein capture beads in the serpentine channel. Scale bar is 200 μm. (D) Plot of the minimum flow distance required for uniform mixing as a function of flow rate ranging from 0.5 to 6 μL/min. Inset: fluorescence images taken at various distances along the channel for mixing a stream of 0.1 μM FITC-BSA solution with the bead suspension co-flowing at the same flow rate. (E) The effect of incubation time on chemifluorescence detection using alkaline phosphatase and the substrate DiFMU. (F) Calibration of on-chip capture and detection of IGF-1R and p-IGF-1R.

This disclosure includes as an illustrative embodiment analysis of exosomes, which generally illustrates the device and sample testing, but the embodiments described in this disclosure can be used and/or adapted for use with any membranous structures that contain immunologically detectable markers. In various embodiments the membranous structures are generally spherical lipid containing bodies. The spherical membranous structure can comprise lipid bilayers. The method is particularly suited for analyzing those membranous structures that are shed or otherwise secreted from cells. Thus, the membranous structures can be derived from any membrane containing biological material, which includes but is not necessarily limited to internal cellular membranes, vesicles, such as secretory vesicles, organelles, enveloped structures, plasma membranes and the like. In certain embodiments, the membranous structure is selected from vesicles, exosomes, microvesicles, microparticles, intraluminal vesicles, endosomal derived vesicles, multivesicular bodies, and combinations thereof. In particular embodiments, the disclosure relates to analysis of exosomes, including but not necessarily limited to plasma-derived circulating exosomes. In certain approaches, exosomes are characterized by exosome surface markers, such as CD9, CD81, and CD63, and combinations thereof. In certain approaches, the exosomes are characterized according to the features described in FIG. 4 presented herein.

In embodiments, the marker that is analysed using a microfluidic device as further described herein is a protein marker. In embodiments, the protein marker is a cancer marker. In an illustrative embodiment which demonstrates feasibility of applying the present disclosure to a wide range of conditions which are positively correlated with the presence of a protein marker, the disclosure includes a demonstration using a protein marker that is characteristic of non-small cell lung cancer (NSCLC). In embodiments, the protein marker is type 1 insulin growth factor receptor (IGF-1R). In embodiments, a microfluidic device as described herein is used to determine the expression levels of total and phosphorylated IGF-1R in NSCLC plasma-derived circulating exosomes. Thus, the disclosure includes a method of diagnosing, or aiding in the diagnosis of, or for monitoring the treatment of an individual diagnosed with, suspected of having, or at risk for developing a condition that is positively correlated with a particular protein marker, such as IGF-1R in connection with NSCLC. The method generally comprises obtaining a biological sample comprising membranous structures, such as exosomes, and analyzing the biological sample using a microfluidic device as described herein for IGF-1R, or any other marker, and/or to determine the expression levels of total and phosphorylated IGF-1R, or any other marker, in NSCLC plasma-derived circulating exosomes, or an exosome-containing sample from an individual who has, or is suspected of having, or has been diagnosed with any other disorder that is correlated with the presence of a marker that is physically associated with the exosomes. In embodiments, a determination of the expression levels of total and phosphorylated IGF-1R in NSCLC plasma-derived circulating exosomes comprises a diagnosis of NSCLC, and/or aids in a physician's diagnosis of NSCLC, and/or is used in staging NSCLC, and/or is used to generate a prognosis and/or treatment protocol for NSCLC, and/or is used multiple times over a period of treatment to assess the efficacy of a treatment. Those skilled in the art will recognize that, instead of IGF-1R, any other immunologically detectable markers can be assayed using a device of the disclosure.

One embodiment of a microfluidic chip of the present disclosure has two capture chambers. A first capture chamber is configured for immunomagnetic isolation and is connected to a sample inlet and a buffer inlet. In one example, the first capture chamber is configured to isolate magnetic microbeads with bound exosomes from a fluid sample. A second capture chamber is configured for protein analysis. The two capture chambers are connected by a first microchannel, a serpentine microchannel, and a second microchannel. The first microchannel and second microchannels may be parts of the serpentine microchannel (such as at the ends of the serpentine microchannel) or may be separate microchannels. The first microchannel connects the first capture chamber to the serpentine microchannel. The second microchannel connects the serpentine microchannel to the second capture chamber. At least one connector channel may be connected to a bead inlet and also to the first microchannel upstream of the serpentine microchannel and downstream of the first capture chamber. A second connector channel with similar connections also may be used. A reagent inlet is connected to the second microchannel upstream of the second capture chamber and downstream of the serpentine microchannel. An outlet may be connected downstream of the second capture chamber.

The first capture chamber and the second capture chamber can be 1-10 mm in diameter, including all integers and ranges of integers there between. In one embodiment, the first and second chambers are approximately 4 mm in diameter and may be configured to each capture a plurality of beads. In embodiments, the first and second capture chambers are configured to capture up to approximately $10^9$ microbeads. In embodiments, the microbeads have a diameter that is less than 10 μm, and is between 0.1 and 10 μm, including all integers there between to the first decimal place, and all ranges of such integers and decimal places. In a non-limiting example, the microbeads have a diameter of 2.8 μm. The connector channel has dimensions configured to let magnetic microbeads pass through. The serpentine microchannel may have a surface that is hydrophilic.

A magnet can be positioned opposite a surface of the microfluidic chip. This microfluidic chip is fabricated using any suitable solid support as a substrate, one non-limiting example of which is a glass substrate. The glass substrate can be modified, such as being fully or partially coated with any suitable polymeric organosilicon compounds, commonly referred to in the art as silicones. In one embodiment, the organosilicon compound comprises a layer of poly (dimethylsiloxane).

A syringe pump, such as a syringe pump with picoliter resolution, can be connected to one of the sample inlet, the buffer inlet, the bead inlet, or the reagent inlet. Alternatively, a four-syringe pump may be connected to the sample inlet, the buffer inlet, the bead inlet, and the reagent inlet.

In another aspect the present disclosure comprises kits. The kits can be provided with the microfluidic device described above, and can further comprise one or more sealed or sealable containers in which are held reagents for obtaining, processing, and using a biological sample, and/or reagents used to isolate, concentrate and/or purify exosomes. In embodiments the reagents comprise one or more buffers, such as buffers for mixing with a biological sample and/or separated exosomes. The kits can also comprise beads, such as glass beads or beads made from other material, such as polymers, i.e., polystyrene, silica, or metals, such as nanometric-sized iron oxide particles, which may be encapsulated or otherwise held together with polymers. In embodiments the beads are magnetized, and may exhibit superparamagnetism in the presence of an externally applied magnetic field. The beads may be modified so that they are suitable for attaching any desired capture agent. Capture agents include but are not necessarily limited to antibodies and antigen binding fragments thereof. In embodiments, the beads are functionalized so that they can be covalently or non-covalently associated with a capture agent. In embodiments, the beads as provided with the kit comprise, for example, streptavidin covalently coupled to the surface of the beads, and as such are configured to form complexes with a biotinylated component, such as a biotinylated antibody or antigen binding fragment thereof. In an embodiment, the beads are coated with a monolayer of streptavidin. In embodiments the beads comprise functionalized groups on their surfaces, or chemical groups that are capable of being functionalized. In one embodiment the beads comprise polyvinyl alcohol on their surface. In embodiments, the beads can be hydrophilic and/or negatively charged. In embodiments, the kits comprise reagents for coupling a capture agent, such as an antibody or antigen binding fragment thereof, to the beads. In embodiments, the beads are configured such that they have an antibody capacity of ~10 μg antibody per 1 mg of beads. In embodiments, the beads can be provided pre-loaded with one or more capture agents pre-loaded onto their surfaces so that they can be used with the microfluidic devices to capture exosomes or any other membranous structure that comprises one or more biomarkers for which the one or more capture agents are specific. In one embodiment, a first set of capture beads is included and may adapted to capture exosomes or an exosome sub-population, regardless of their biomarker content. Thus, the beads can be covalently modified to comprise an exosome specific binding partner, such as an exosome specific antibody. In embodiments, the beads comprise antibodies that bind with specificity to the exosome markers CD9, or CD81, or CD63, or Epithelial cell adhesion molecule (EpCAM), or combinations thereof. Combinations of these markers present on one, or distinct combinations of beads are also encompassed by this disclosure. In embodiments, a capture agent for CD63 is used in addition with at least one other exosome capture agent. In an alternative embodiment, no capture agent directed to CD63 is used. Variable capture agents can be used in this embodiments corresponding to measurement configuration.

A second set of capture beads can also be provided, and can be adapted for capturing and/or detecting one or more biomarkers, such as a protein biomarker, including but not limited to a protein known to be associated with a particular disorder, such as one or more types of cancer. Thus, in various embodiments, the kits comprise exosome capture beads, and may further comprise beads for biomarker capture, wherein the biomarker is distinct from the exosome marker.

The following examples are presented to illustrate the present disclosure. They are not intended to be limiting in any manner.

Example 1

Figure 1:
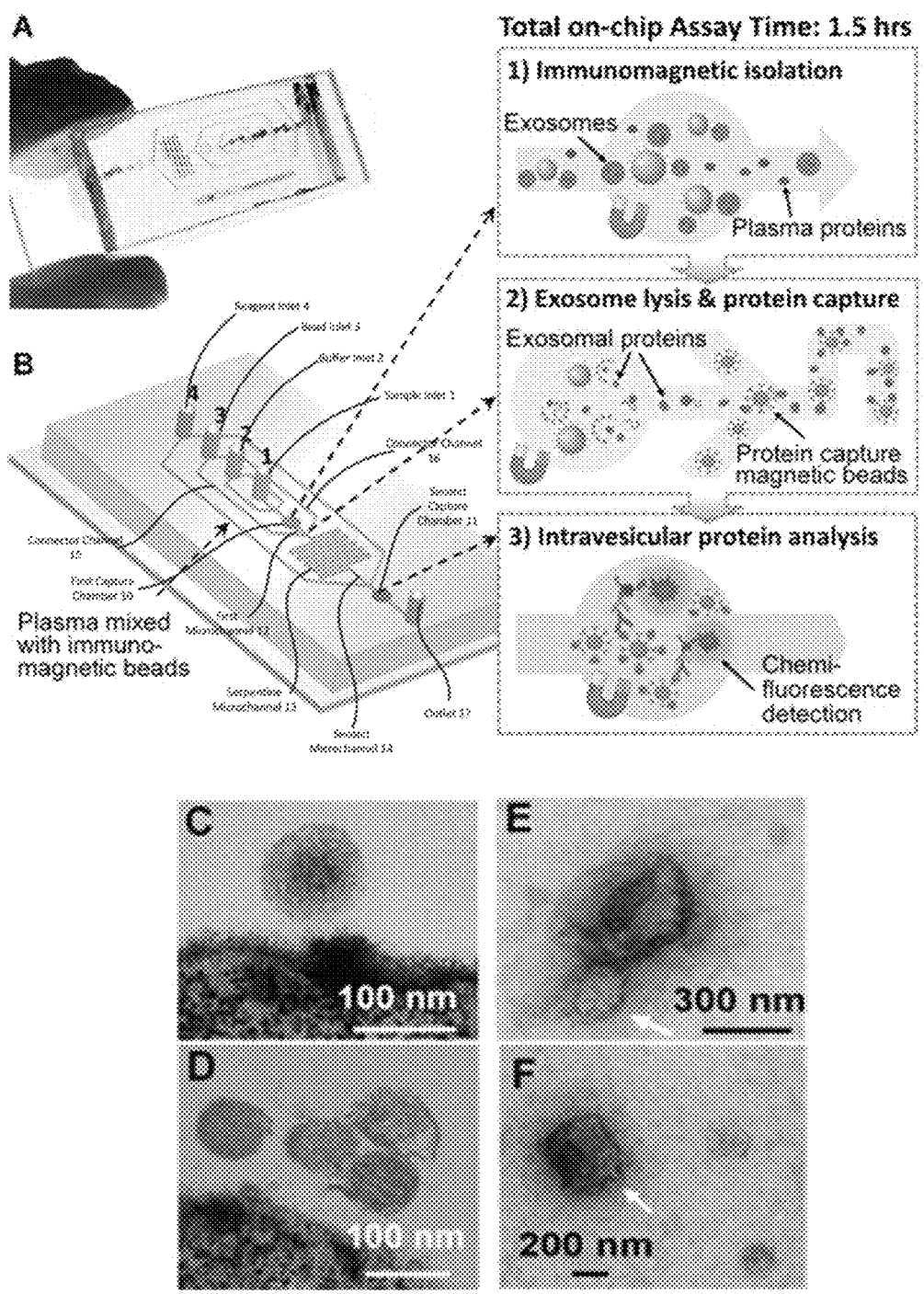
FIG. 1 shows an example of an integrated microfluidic exosome analysis directly from human plasma. (A) Image of the prototype PDMS chip containing a cascading microchannel network for multi-stage exosome analysis. (B) Streamlined workflow for on-chip immunomagnetic isolation, chemical lysis, and intravesicular protein analysis of circulating exosomes. #1-4 indicates the inlet for exosome-capture beads, washing/lysis buffer, protein-capture beads, and ELISA reagents, respectively. (C, D) Typical TEM images of exosomes from NSCLC (C) and ovarian cancer plasma (D) isolated by the microfluidic immunomagnetic method. The magnetic beads were conjugated with anti-EpCAM and anti-CA125 antibodies for NSCLC and ovarian cancer, respectively. (E, F) TEM images showing large aggregates (E) and other membranous particles (F) observed in the ultracentrifugation-purified vesicles, as indicated by white arrows.

This and the following Examples relate to integrated microfluidic microvesicle profiling using an illustrative device which contains a cascading microchannel circuit to integrate and streamline the multi-step profiling of exosomes directly from human plasma, including exosome isolation and enrichment ($1^{st}$ stage capture), exosome lysis, fluidic mixing and immunomagnetic capture of intravesicular targets ($2^{nd}$ stage capture), and protein assays (FIG. 1). A representative device architecture is detailed in FIG. 1A. The two cascading magnetic-bead capture chambers (first capture chamber 10 and second capture chamber 11) are of 4-mm diameter and are capable of capturing up to $10^9$ 2.8

µm microbeads each. A plasma sample pre-mixed with antibody labeled magnetic beads is introduced through sample inlet 1 into the first capture chamber 10 where the magnetic beads with bound exosomes are isolated from the sample and washed by PBS washing buffer (FIG. 1B). The lysis buffer is introduced through the buffer inlet 2 and incubated with captured exosomes in the first capture chamber 10 by stopping the flow. The lysate then flows into a first microchannel 12, a serpentine microchannel 13, and a second microchannel 14 along with antibody labeled magnetic beads introduced from a bead inlet 3 into two connector channels 15, 16 to specifically capture released intravesicular proteins (FIG. 1 B (2)). The protein capture beads are magnetically retained in the second capture chamber 11 in which detection antibodies (bead inlet 3) and chemifluorescence reagents (reagent inlet 4) can be introduced to perform sandwich immuno-detection of captured intravesicular protein markers (FIG. 1 B (3)). The complete analysis can be finished with as low as 30 µL plasma samples in ~2 hrs, i.e., 0.5 hrs for sample incubation with magnetic beads and ~1.5 hrs for the on-chip assay. A sample can flow from the second capture chamber 11 to an outlet 17 for collection. The multiple fluidic introductions are precisely controlled using programmable syringe pumps with picoliter resolution, though other types of pumps also may be used.

A representative transmission electron microscopy (TEM) image of on-chip immunomagnetically isolated plasma exosomes is shown in FIG. 1C, in comparison to ultracentrifugation-purified plasma microvesicles (FIGS. 1D and E). Immunomagnetic isolation revealed a population of vesicles in a typical round, homogenous morphology with a major size distribution of 40-150 nm, consistent with reported exosome morphology. The cup-shaped morphology is often considered erroneously as a typical appearance of microvesicles resulted from membrane collapse during sample drying, without embedding and sectioning for TEM imaging. Relatively large aggregates and other membranous particles (see arrows in FIGS. 1D & E) in a heterogeneous population of vesicles purified by ultracentrifugation could be observed in some samples. Although ultracentrifugation is the most commonly used technique to isolate exosomes, the limitation in differentiating the subpopulation of extracellular vesicles highlights the need for the present, more selective isolation approach.

Figure 6:
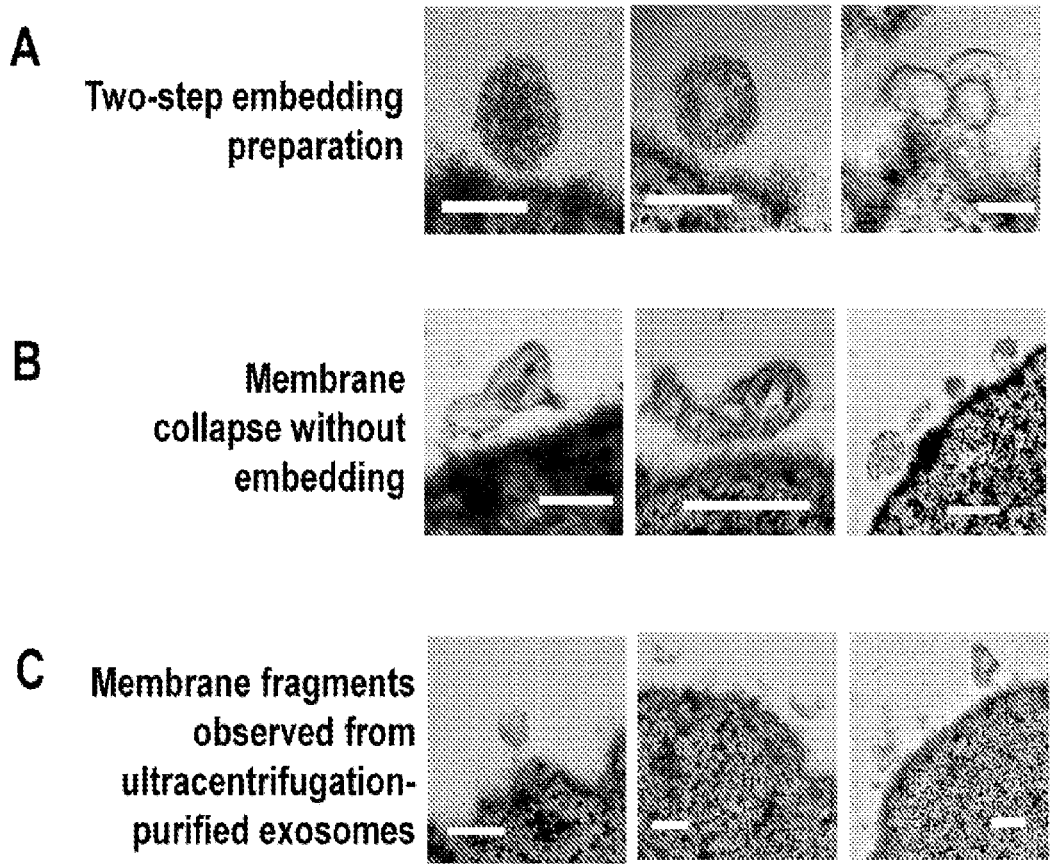
FIG. 6. TEM representations of sample preparation steps. The sample preparation approaches significantly affect the exosome morphology and integrity. Representative images were analyzed by transmission electron microscope. (A) The exosomes immune-captured by micro-sized magnetic beads were prepared by two-step embedding protocols prior imaging. The fully intact and regular round shape was observed as the typical appearance of exosomes. (B) Membrane collapse was observed from exosomes prepared without embedding prior imaging. The irregular shape and cup shape were observed due to collapse during sample drying. (C) Collapsed exosomes and membrane fragments were often observed when immunomagnetically capturing the plasma-derived vesicles pre-isolated by differential ultracentrifugation. It may be attributed to the high shear force and mechanical damage that occur during ultracentrifugation. The scale bar is 100 nm.
Figure 7:
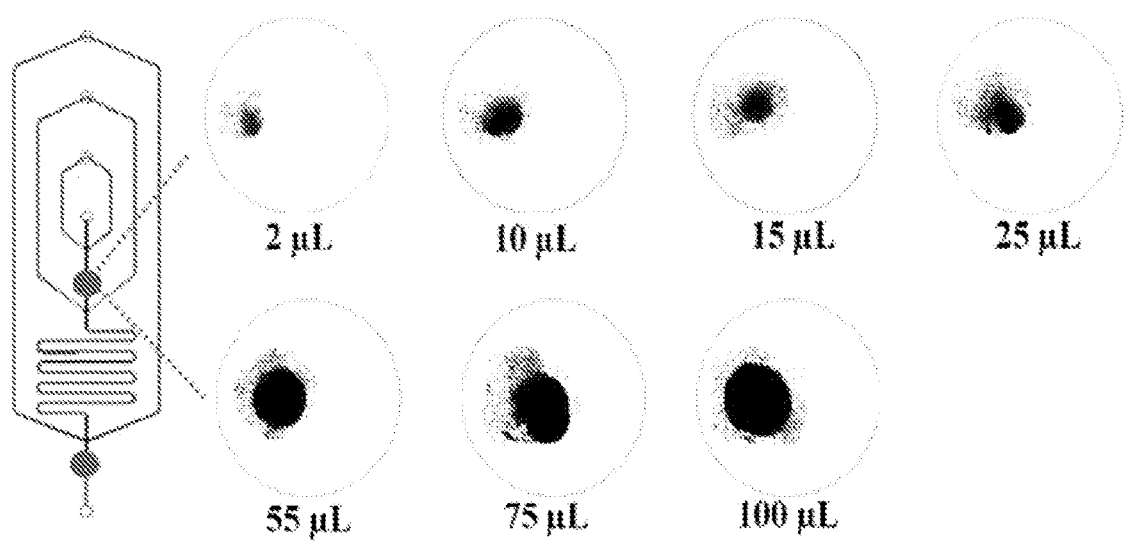
FIG. 7. Graphical depiction and SEM representations beads. The beads suspended in a buffer solution were infused into the chamber and retained by the magnet placed underneath the center of the chamber, forming a field-induced aggregate due to the dipolar interactions between the beads. The size of immobilized micro-bead aggregates grows in the chamber near a magnet underneath with the increase of infused sample volume. The bright field images of aggregates in the magnetic capture chamber were acquired and analyzed using ImageJ to calculate the aggregate size relative to the chamber size.

In more detail as it relates to FIG. 1, our microfluidic technology uses the magnetic bead-based strategy to integrate and streamline the multi-step analysis of exosomes directly from human plasma (FIG. 1A). Compared to the surface-based exosome microchips, the immunomagnetic method allows for enrichment of captured exosomes and convenient sample preparation for TEM characterization, in addition to higher capture efficiency and analysis sensitivity due to larger surface area. As described above, the PDMS chip of this disclosure uses a cascading microchannel circuit to sequentially conduct exosome isolation and enrichment (1st stage capture), chemical lysis, immunoprecipitation of intravesicular targets (2nd stage capture), and chemifluorescence-assisted sandwich immunoassay (FIGS. 1A and 6 Table 2). Briefly, to create portions of FIG. 1, plasma sample pre-mixed with antibody labelled magnetic beads was introduced through the inlet #1 into the first chamber where the magnetic beads were retained and washed by PBS buffer (FIG. 1B) (1), FIG. 18). A lysis buffer was then introduced through the inlet #2 to fill the chamber and then the flow was stopped to incubate with the captured exosomes. The lysate was flowed into a serpentine channel along with the antibody labelled magnetic beads injected from two side channels to capture intravesicular proteins released (FIG. 1B (2)). The protein capture beads were magnetically retained in the 2nd chamber where detection antibodies and chemifluorescence reagents were sequentially introduced to perform sandwich immuno-detection of protein markers of interest (FIG. 1B (3)). The buffers for binding and washing have been optimized to minimize bead aggregation and non-specific adsorption while maintaining the integrity of captured exosomes (see FIG. 6). The on-chip assay can be completed in less than 1.5 hrs and uses as low as 30 µL plasma sample. FIGS. 1C & D show representative TEM images of on-chip isolated exosomes from NSCLC and ovarian cancer (OVCA), respectively. We observed a typical round, homogenous morphology of exosomes which were carefully prepared by embedding and sectioning for TEM imaging. The cup shape of exosomes was often observed by electron microscopy, which is likely resulted from drying-caused collapse of vesicles. A major size distribution of 40-150 nm was determined, which is consistent with the reported size range. For comparison, we purified the exosomes by the gold standard method, ultracentrifugation, and often observed a heterogeneous population of vesicles containing relatively large aggregates and other membranous particles (FIGS. 1E & F). It is notable that at the early stage of technical development, we also explored the immunocapture of ultra-centrifugation-purified exosomes for parallel evaluation of the one-step microfluidic isolation. However, the capture efficiency was found considerably low and variable, which may be attributed to the fact that the recovery rate of ultra-centrifugation is low (5-25%) and further reduced by the additional immunocapture steps. In addition, we observed much more irregular vesicles bound to the beads by TEM, which appear to be collapsed or damaged (FIG. 6).

Example 2

Figure 2:
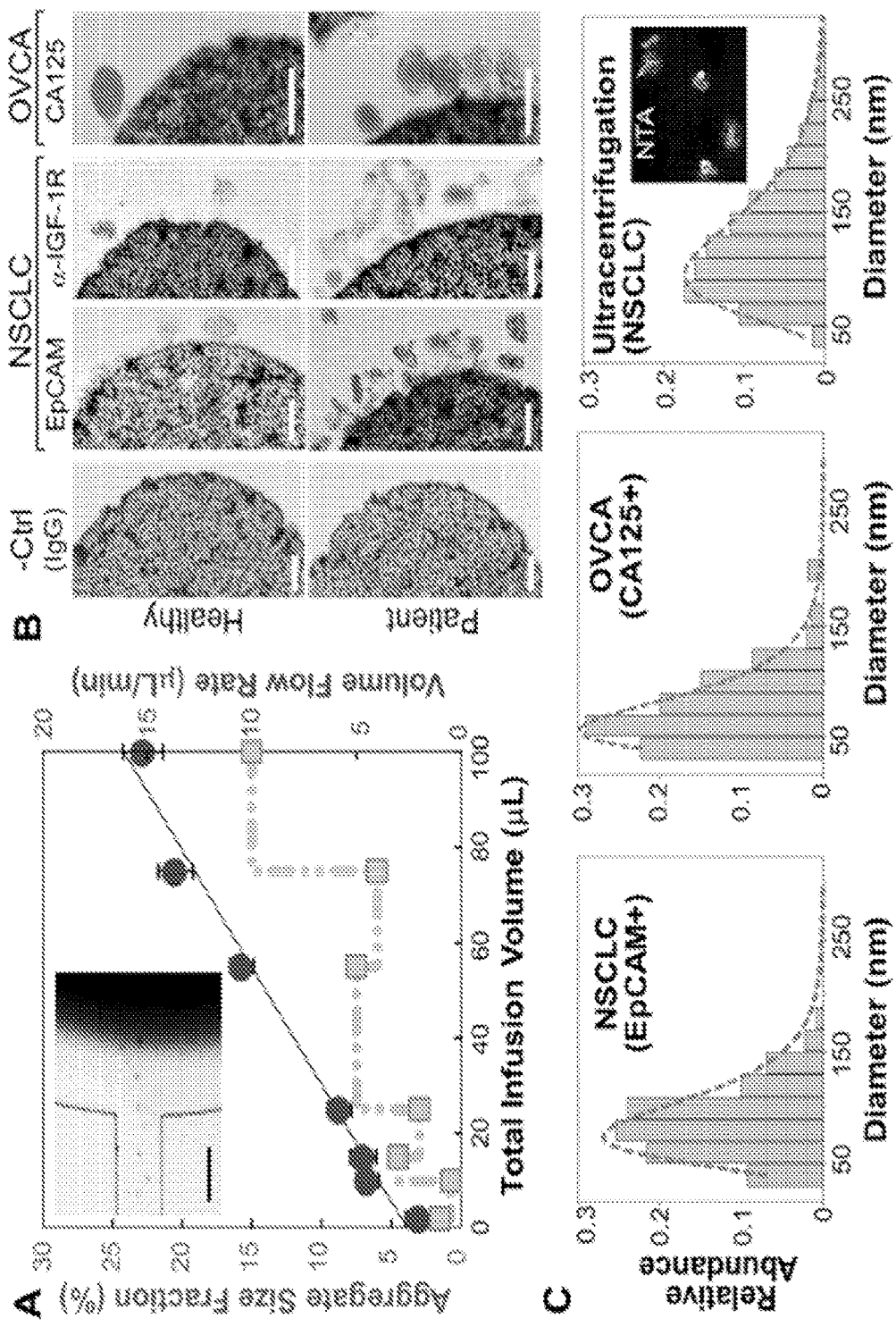
FIG. 2. Microfluidic immunomagnetic capture of circulating exosomes. (A) Plot of the amount of beads captured in the chamber represented by the aggregate area fraction as a function of total infusion volume (circle) and flow rate (square). The error bars are standard deviations (n=3). Inset: bright-field image of capturing magnetic beads in the 1st capture chamber. Scale bar is 100 μm. (B) Representative TEM images showing enriched exosomes on the surface of antibody-conjugated beads from NSCLC and ovarian cancer (OVCA) samples, while significantly less vesicles from healthy plasma and almost no vesicles for the negative control beads without specific antibodies. (C) Representative size histograms for on-chip isolated exosomes from NSCLC (EpCAM+, n=130) and OVCA (CA125+, n=130), compared to that of ultracentrifugation-purified NSCLC vesicles measured by NTA using NanoSight (insets). The size was obtained from averaging five measurements. Dot plots are Log-normal fitting ($R^2$>0.98). Scale bars: 100 nm.

This Example provides a description of on-chip immunomagnetic isolation of circulating exosomes. We first investigated magnetic capture of beads as it dictates the overall performance of exosome isolation and analysis. The beads suspended in a buffer solution were retained by a magnet placed underneath the capture chamber (FIG. 2A, inset), forming an aggregate (FIG. 8) induced by the dipolar interactions between the beads. It was reported that the amount of magnetically captured beads in a microchannel can be represented by the size of the bead aggregate, which increases linearly with time at a constant flow rate. We adopted this approach to conveniently assess the bead capture a function of flow conditions (FIG. 2A). It was found that the aggregate size was linearly dependent on the total sample infusion volume regardless of the flow rates applied to reach certain infusion volumes (1-10 µL/min, FIG. 2A). The independence on flow rate indicates a high bead capture efficiency and capacity of our system, which ensures quantitative measurement of exosomes over a wide range of flow conditions and sample volume. We chose low flow rates for affinity capture of exosomes and protein targets released by chemical lysis (2 µL/min and 1 µL/min, respectively), at which the bead recovery efficiency was determined to be >99.9% by counting the residual beads in the eluent.

Figure 9:
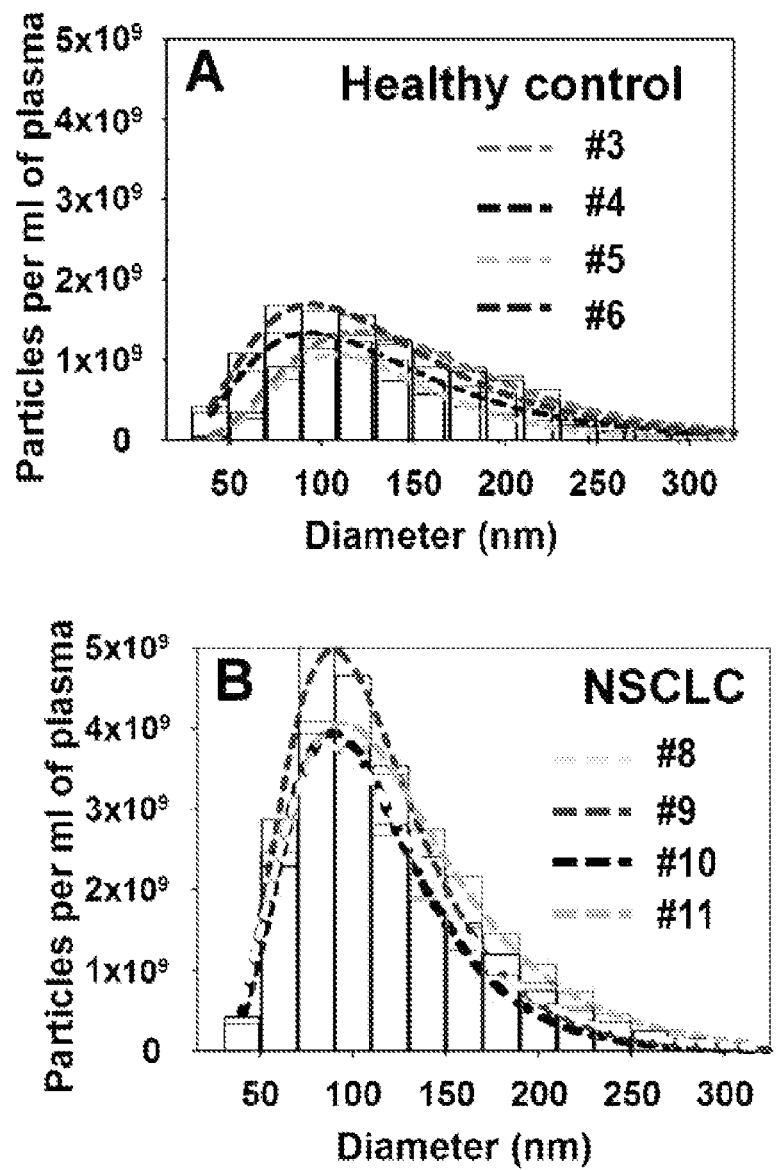

To verify the capture specificity and generalizability of our method, we compared the on-chip purification of exosomes from NSCLC, OVCA, and healthy plasma using beads labeled with the monoclonal antibody specific for epithelial cell adhesion molecule (EpCAM), IGF-1R α unit (α-IGF-1R) or CA125. TEM examination shows that the antibody beads were densely coated with vesicles from the patient sample, while significantly less vesicles from healthy plasma and almost no vesicles for the negative control beads without specific antibodies. These results confirm the specific binding of exosomes and effective washing to minimize non-specific binding. Moreover, we examined by TEM numerous exosomes isolated by targeting various surface markers. The majority of those exosomes remained intact, in contrast to much more damaged vesicles observed for immunocapture of vesicles pre-purified by ultracentrifugation (FIG. 9). This indicates the advantage of the direct one-step microfluidic immunoisolation to preserve vesicle integrity over the conventional ultracentrifugation-based protocols.

Figure 8:
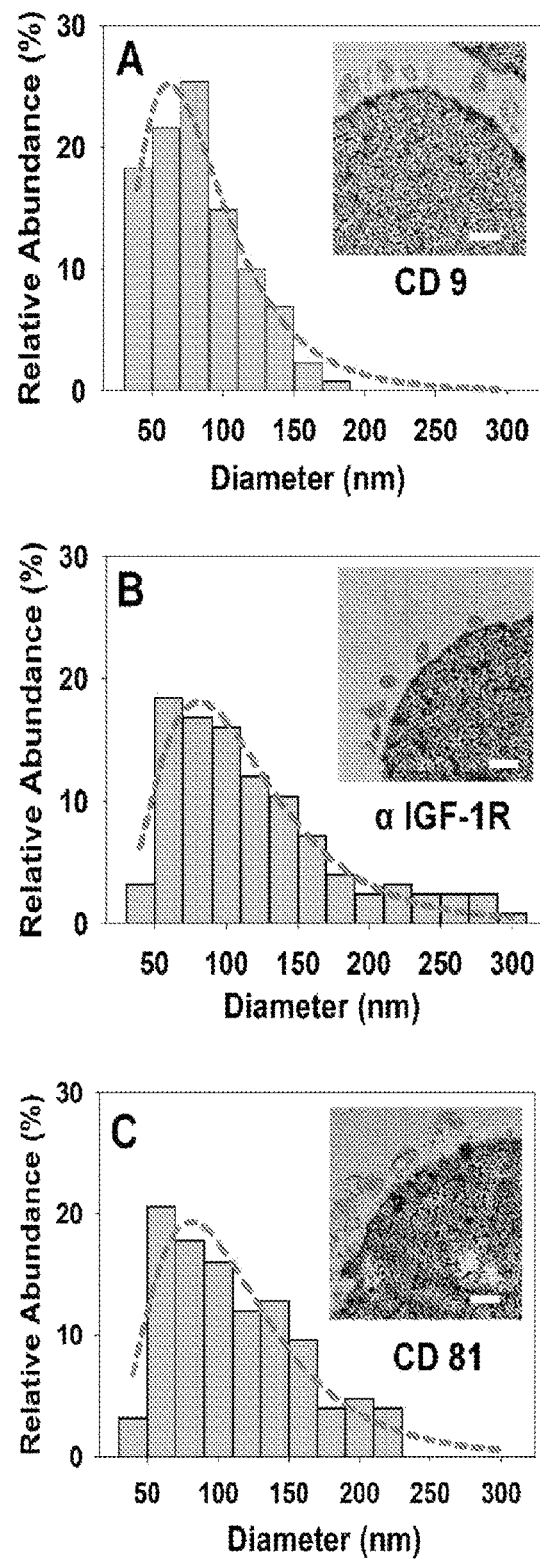
FIG. 8. Graphs showing size distributions of exosomes isolated from NSCLC plasma by the microfluidic immuno-magnetic capture targeting exosomal surface proteins (A) CD9, (B) α-IGF-1R, and (C) CD81, respectively. 130 captured vesicles were measured for each marker. Insets: representative TEM images of exosomes from each subpopulation. Scale bar is 100 nm. The dotted red lines are Log-normal fitted plots ($R^2>0.98$). It was found that the percentages of the vesicles smaller than 150 nm are ~97%, 80%, and 82% for CD9+, α-IGF-1R+, and CD81+ subpopulations, respectively FIG. 9. Graphs showing size distribution of circulating exosomes from NSCLC and control subjects tested in FIG. 5 (main text) using ultracentrifugation purification and NTA (NanoSight). There is no distinct size profiles between healthy and NSCLC exosomes isolated by ultracentrifugation (fitted using log-normal distribution, $R^2>0.98$).

The on-chip capture performance was further characterized by the size distribution of individual exosome subpopulations isolated by targeting both tumor-associated markers (EpCAM, α-IGF-1R, and CA125) and common exosomal markers (CD9, CD81, and CD63). Size is the most acceptable criterion for exosome identification and differentiation from other extracellular vesicle types. Current consensus is that exosomes originated from multivesicular endosome fusion are typically smaller than 150 nm while the majority of microvesicles derived from plasma membrane are relatively larger (150-2000 nm). Compared to nanoparticle tracking analysis (NTA) by NanoSight which requires ~1 mL of concentrated vesicles (~$10^9$ mL$^{-1}$) for accurate size determination, TEM provides a robust means for sizing and counting of exosomes in small-volumes collected from microfluidic isolation without significant dilution (~30 μL). Most immunocaptured exosomes were found smaller than 150 nm with notably smaller size range (e.g., 97% of EpCAM+ and CA125+ vesicles <150 nm) than that of ultracentrifugation (72.1%) (FIG. 2C and FIG. 8). Current "gold standard" approaches based on ultracentrifugation pull down a mixed population of various extracellular vesicle types with a wide size distribution. Indeed, our NTA analysis of ultracentrifugation-purified vesicles yielded broader size variation and no distinct profiles between healthy and NSCLC cases (FIG. 2C and FIG. 9). These findings indicate the microfluidic immunocapture method of this disclosure provides a more specific approach to purifying exosomes than ultracentrifugation.

Example 3

Figure 3:
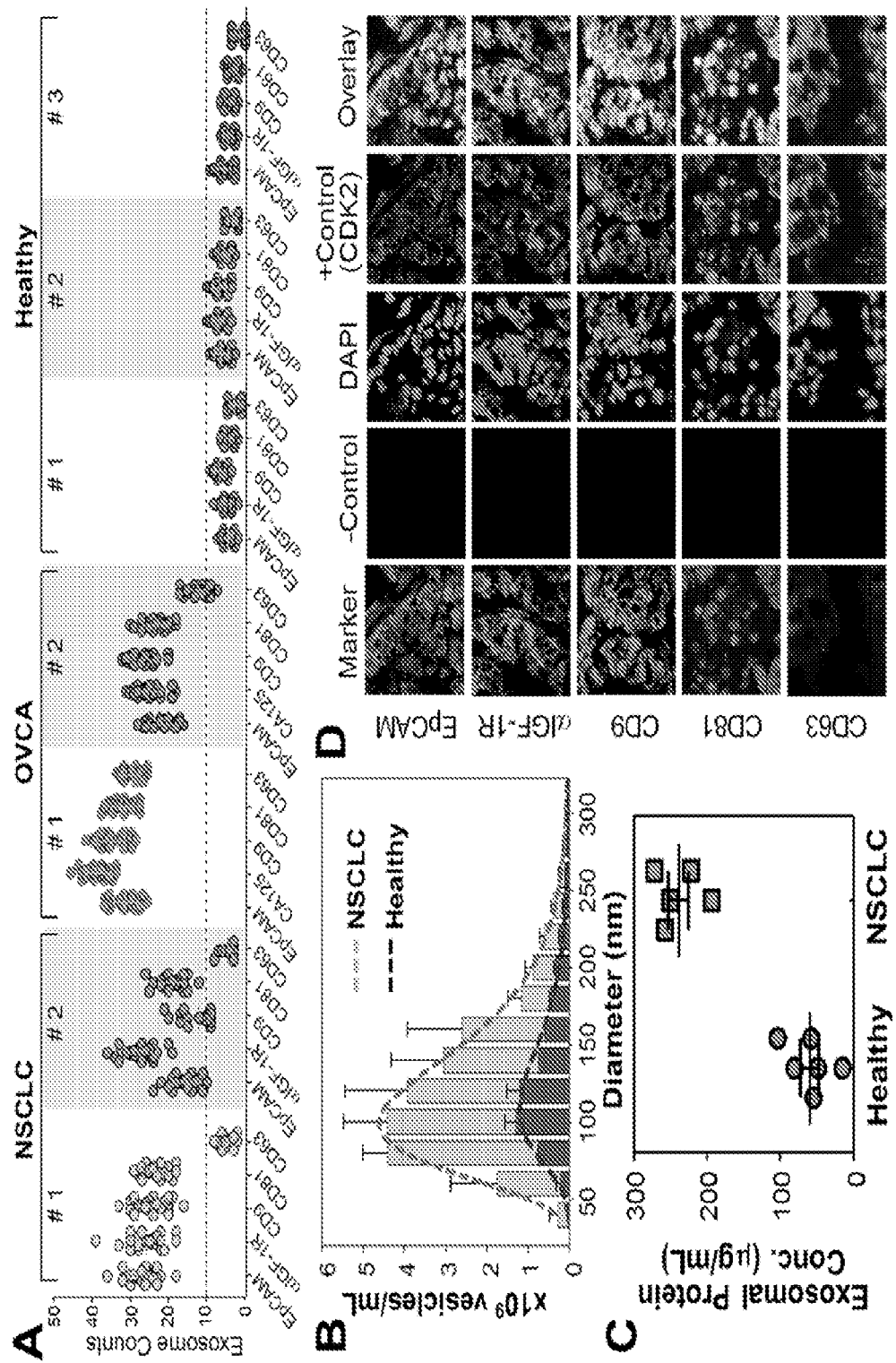
FIG. 3. Microfluidic isolation and surface phenotyping of circulating exosomes in cancer. (A) The scattered dot plot of the abundance of bead-bound exosomes from NSCLC, OVCA and healthy plasma obtained by TEM (n=25). A panel of surface markers (EpCAM, α-IGF-1R, CA125, CD9, CD81 and CD63) were used for exosome isolation. Dash line indicates the highest exosome counts observed for healthy controls. (B) NTA analysis of size distribution and abundance of vesicles purified from NSCLC and healthy controls by ultracentrifugation. The error bars are the standard deviations. Dashed lines are Log-normal fitting ($R^2$>0.98). (C) Bradford assay of total protein in ultracentrifugation-purified exosomes from NSCLC patients (stage II) and healthy subjects (p=0.0007). (D) Representative IFH images of the matched tumor tissue from NSCLC patient #1 in (A) showing high expression of the biomarkers except CD63
Figure 10:
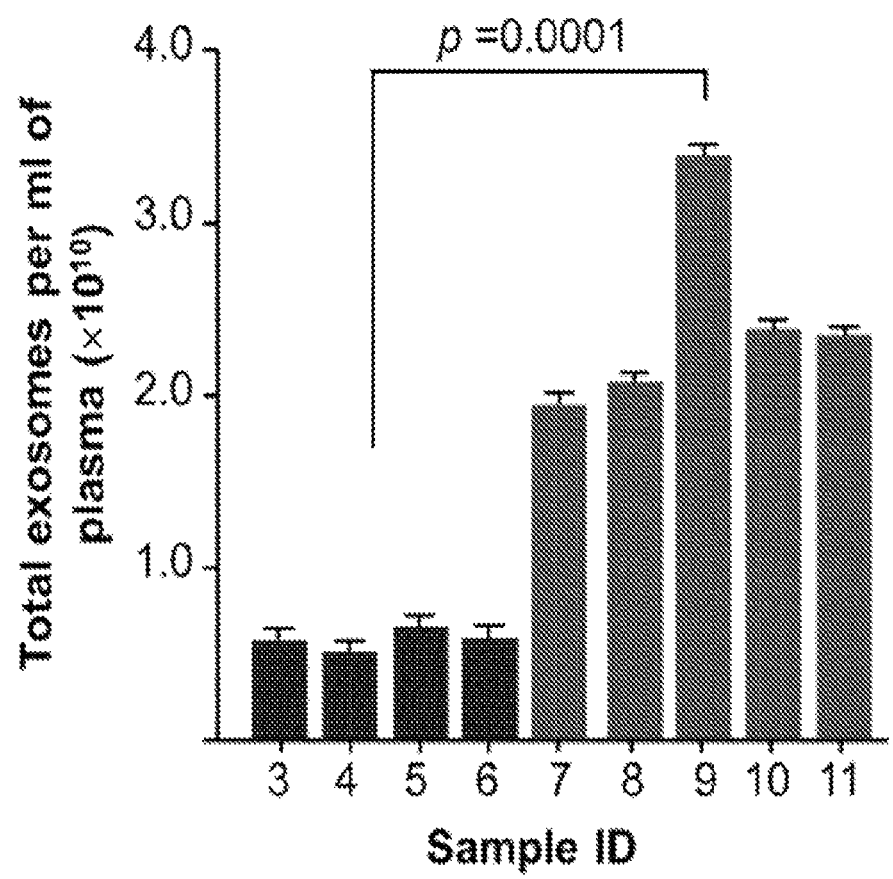
FIG. 10. Graph showing total circulating exosomes in the plasma of healthy donors (blue) and NSCLC subjects (red) in Figure S4 measured by NTA (NanoSight). The results are presented as the total number of particles per milliliter of plasma. Error bars represent the standard deviations of five measurements. NSCLC patient plasma samples contain significantly higher concentration of exosomes than that of the healthy controls (p=0.0001).
Figure 11:
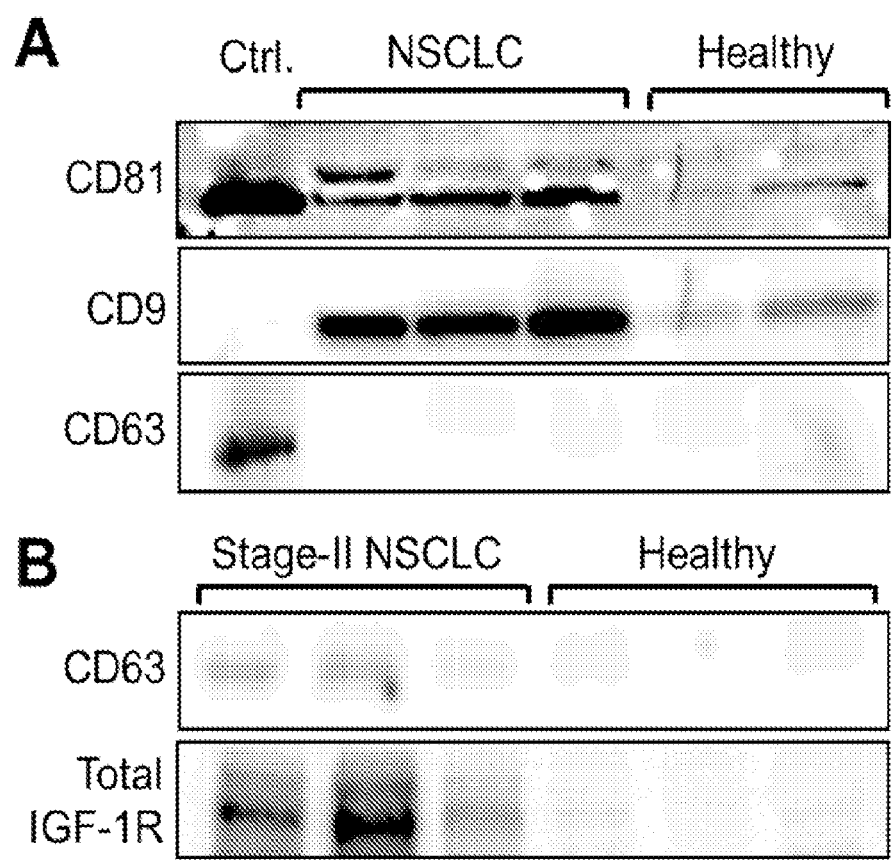
FIG. 11. Western blot analysis of ultracentrifugation-purified exosomes. (A) Differential expression of CD81 and CD9 and low expression of CD63 in exosomes from NSCLC cases of various stages (from left to right, I, VI and II) versus healthy controls. Exosomes purified from an ovarian cancer cell line C30 was included as the positive control for CD63 expression. (B) Western blot analysis of more Stage II NSCLC patients shows consistently low expression of exosomal CD63, which further confirms the observation in the main text (FIG. 3). NSCLC plasma exosomes showed higher expression of total IGF-1R than in the healthy controls, which verifies the on-chip results obtained by using the same samples (FIG. 5).
Figure 12:
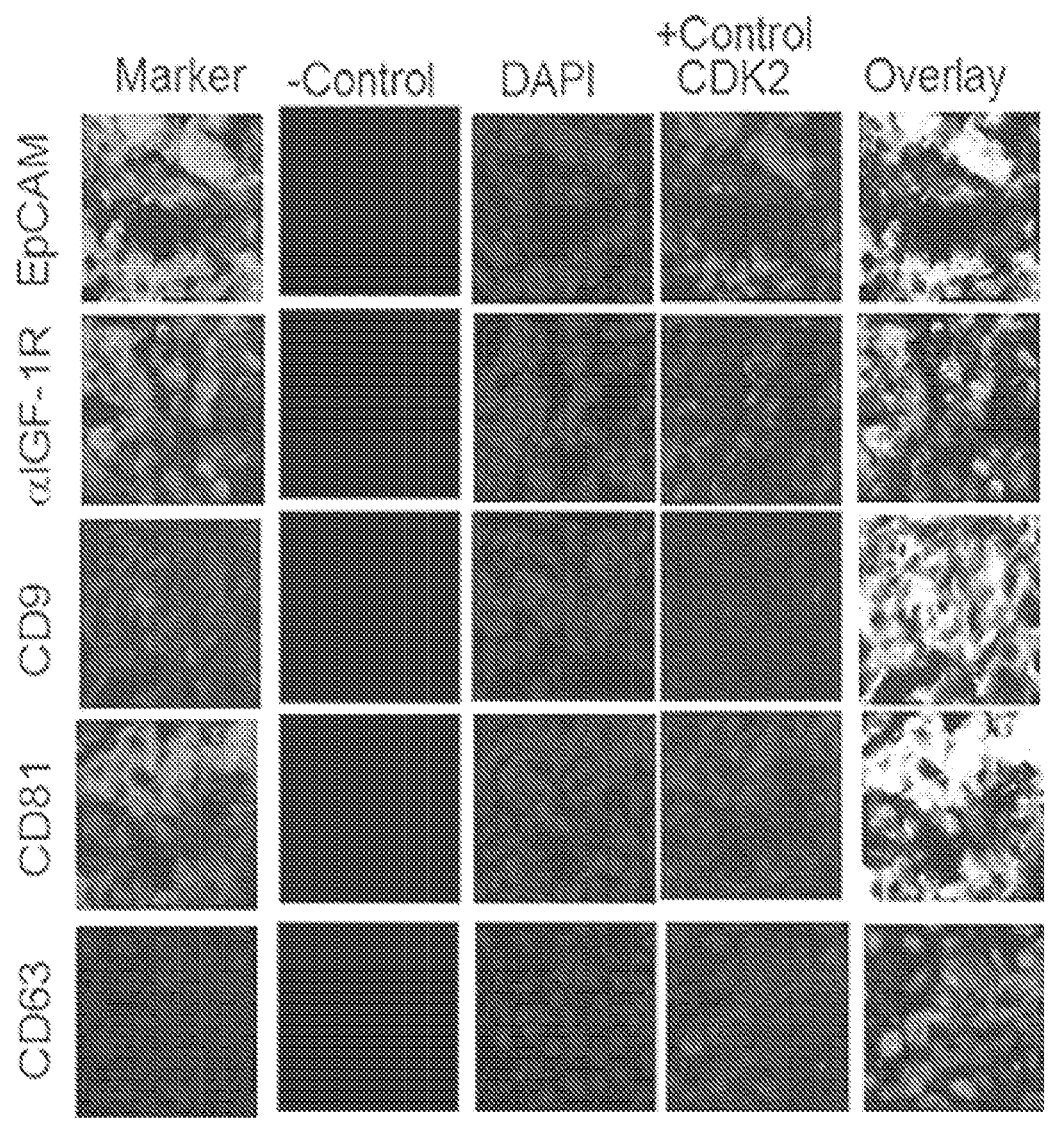
FIG. 12. Three-color IFH images of tumor tissue from NSCLC patient #2 in FIG. 3 in the main text, showing high expression of EpCAM, α-IGF-1R, CD9, CD81 but low expression of CD63. The tumor tissues were biopsied from lower lobe of lung tumor from the matched patient. Images were collected and merged in three-color using Metamorph. The IFH image size is ~12×12 mm.

This Example provides a description of profiling of exosome subpopulations by protein phenotype. Surface protein composition of exosomes plays an important role in exosome-mediated effects and may provide tumor fingerprints. To demonstrate the ability to detect exosomal expression patterns associated with cancer, we conducted relative quantification of five exosome subpopulations defined by individual surface markers using TEM. FIG. 3A exemplifies the results for two of the NSCLC samples that we have tested. Distinct subpopulation landscapes were observed, as compared to the healthy controls with a 3- to 5-fold increase in abundance for the surface markers except CD63. We further demonstrated the adaptability of our method for other cancers by testing on OVCA with the tumor markers (EpCAM and CA125) and exosomal markers (CD9, CD81, and CD63). The OVCA samples also provide a positive control for the NSCLC studies, as CD63 was found to be highly expressed in OVCA exosomes. High CD63 expression was observed, which validates our method and supports the observation of low CD63 expression in NSCLC cases. The abilities to discriminate disease from healthy subjects and to detect differential expression of markers (e.g., CD63) in cancers indicate the high immunocapture specificity of the present microfluidic method. To verify the microfluidic results, we performed parallel analyses of the NSCLC samples using standard ultracentrifugation and analytical methods. Exosome abundance of the patient plasma measured by NTA showed a ~4-fold increase in average than that of the healthy controls (p=0.0001, FIG. 3B and FIG. 10, in line with the total protein levels determined by the Bradford assay (3.9-fold increase in average, p=0.0007, FIG. 3C). Western blotting analysis showed increased exosomal expression of CD9, CD81, and IGF-1R markers, but indiscernible or low CD63 levels in NSCLC patients of various stages (FIG. 11). In this case, the exosomes collected from a cell line (ovarian cancer C30) were included as a positive control for CD63 detection. Collectively, these standard studies verify the microfluidic analysis of surface phenotypes of circulating exosomes. Both microfluidic and the standard methods detected significant elevation of exosome abundance and exosomal markers in NSCLC and OVCA, inferring the potential clinical value of circulating exosomes for cancer research and diagnostics. The present microfluidic technology provides not only a general approach for one-step isolation of exosomes directly from plasma, but also the ability to purify molecularly defined subpopulations that are inaccessible to other physical methods such as ultracentrifugation, nanofiltration and size exclusion. Such capability would be beneficial for deconvoluting the complexity of extracellular vesicles to facilitate molecular classification and characterization of exosomes. The unique one-step isolation system also contrasts with the conventional bulk immunomagnetic methods in that it eliminates multiple, lengthy preparation steps of washing and manual buffer exchange which can cause damage and loss of exosomes. To determine if the plasma-derived exosomes in NSCLC show similar protein profiles to the tumor origin, we conducted the three-color immunofluorescence histological (IFH) study of patient-matched lung tumor tissues. High expression of EpCAM, α-IGF-1R, CD9 and CD81 and low expression of CD63 were detected in the tumor tissues (FIG. 3D and FIG. 12), in agreement with the subpopulation profiles of plasma exosomes obtained by the microfluidic technology and the standard analyses (FIG. 3 and FIG. 11). The matched molecular profiles between circulating exosomes and tumor tissues support the potential use of exosomes for non-invasive molecular profiling of solid tumor tissue. Our studies also provide experiment evidences to support recently arising questioning on the use of CD63 as a general surface marker for exosome isolation. Decreased CD63 expression has been found in relation to tumour growth and invasiveness in lung and other cancers.

Example 4

This Example provides a description of integrated exosome analysis for non-invasive detection of cancer biomarkers. Recent results on profiling of microRNAs contained inside circulating exosomes have demonstrated the potential of exosomes as surrogate markers for tumor biopsy. There is increasing interest in proteomic characterization of exosomes. Our ultimate goal is to develop a microfluidic technology capable of measuring both surface and intravesicular proteins of circulating exosomes. In this proof-of-concept study, we demonstrated the integrated analysis of two targets in NSCLC: total IGF-1R and phosphorylated IGF-1R (p-IGF-1R). The IGF-1R pathway provides a potent proliferative signaling system implicated in tumorigenesis and metastasis. Phosphorylation of IGF-1R initiated by binding of ligands, such as IGF-1, is required for activation of the MAPK, PI3K, AKT and other signaling pathways involved in cell proliferation and survival. Thus there has been an intense interest in studies of IGF-1R and p-IGF-1R as diagnostic markers and therapeutic targets. However, currently immunohistochemistry test of tumor tissues predominates in clinical assessment of IGF-1R expression, which is invasive and problematic for regular monitoring of disease progression and response to treatment. To our best knowledge, no studies of exosomal IGF-1R and p-IGF-1R have been reported. As illustrated in FIG. 4A, IGF-1R is a transmembrane protein composed of two surface α subunits and two intravesicular β subunits containing tyrosine kinase domain which can be phosphorylated. Thus the total IGF-1R and p-IGF-1R provide good model targets for demonstrating microfluidic surface phenotyping and intravesicular protein analysis of exosomes. To avoid the interference from free proteins in plasma, we used a monoclonal EpCAM antibody for exosome capture and two antibodies that specifically recognize α-IGF-1R and p-IGF-1R, respectively.

The unique cascading microfluidic immunocapture strategy described herein enables integration of exosome isolation with downstream processing and analysis, i.e., chemical lysis, flow mixing and protein capture, and chemifluorescence-based sandwich immunoassays. To chemically lyse the captured exosomes, a mild non-ionic detergent, Triton X-100, was used to lyse cells yet to retain the activity of proteins. The lysis conditions, including Triton X-100 concentrations and incubation times, were studied and 5 min incubation with 5% Triton X-100 was found to be sufficient to completely lyse exosomes (FIG. 4B). The exosome lysate was flushed into a serpentine microchannel to mix with magnetic beads conjugated with specific antibody to capture released protein targets. To enhance fluidic mixing, the suspension of protein capture beads was injected from two side channels to flank the lysate stream (FIG. 4C, top), which facilitates the mass transfer across the channel. Uniform bead distribution across the 200-μm channel can be achieved within a travel distance of ~10 mm at 1 μL/min (FIG. 4C, bottom). Fluorescence imaging was also employed to exam the mixing behaviour, which reveals a linear response of the minimum distance for complete mixing to flow rate in the range of 0.5 to 6 μL/min (FIG. 4D). This result provides a guidance to optimize the chip design and flow rate. In our system with a 25-cm mixing channel and 4-mm microchamber, a flow rate of 1 μL/min was used to yield a long incubation time of ~3.8 min which allows efficient solid-phase affinity capture of protein.

Figure 14:
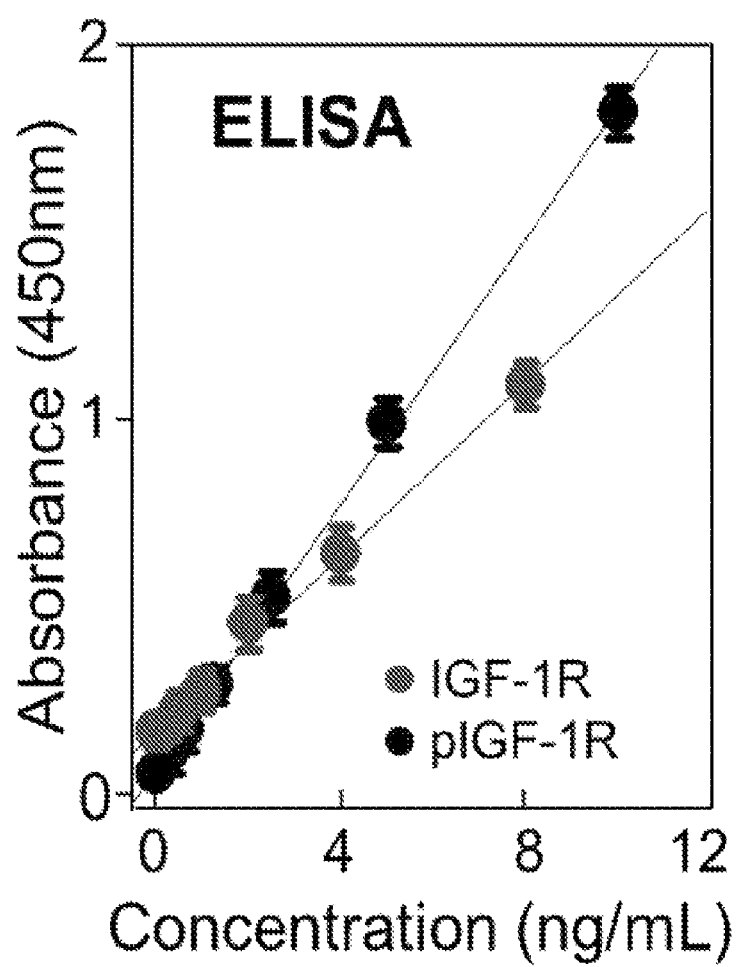
FIG. 14. Graph showing calibration of quantitative detection of total IGF-1R and phospho-IGF-1R using the standard 96-well microplate ELISA kit FIG. 15. Graph showing quantitative detection of exosomal IGF-1R as a function of total exosome concentration in plasma. 10-fold dilutions of a NSCLC plasma sample (patient #11) were assayed to obtain the calibration curve (solid triangles). The measurements of the subjects in the main text FIG. 5 were superimposed in the plot (inset). Error bars are standard deviations (n=5 for x axis and n=3 for y axis).

We then optimized the on-chip bead-based immunoassay and chemifluorescence readout using a matched pair of capture/detection antibodies, alkaline phosphatase (AP) conjugated secondary antibody, and the DiFMUP substrate. The incubation time is an important factor for the small-scale enzymatic chemifluorescence detection. It was found that the fluorescent signal saturates after 6 min incubation in the microchamber (FIG. 4E), allowing for fast on-chip protein detection. We then calibrated the on-chip human IGF-1R and p-IGF-1R assays by running protein standards through the entire process except the lysis step. As plotted in FIG. 4F, the microfluidic assay achieved quantitative detection of IGF-1R and p-IGF-1R over a dynamic range of 4 logs with a detection limit of 0.281 pg/mL and 0.383 pg/mL, respectively (S/N=3). Such sensitivity is at least 100-fold higher than the commercial ELISA kits (FIG. 14), which indicates efficient immunoprecipitation of exosomal proteins in our microfluidic system.

Figure 5:
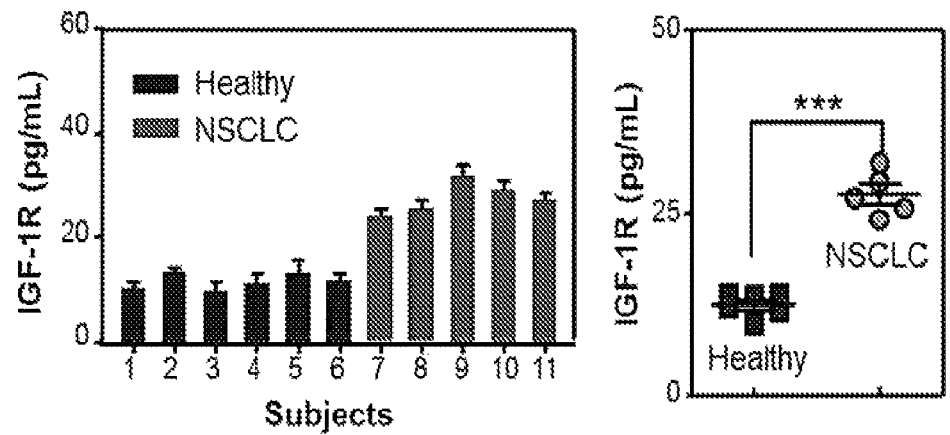
FIG. 5. Quantitative detection of total IGF-1R in circulating exosomes directly from clinical plasma samples. (A) The results of the integrated microfluidic analysis presented in the bar (left) and scattered dot (right) plots show significant overexpression of IGF-1R in EpCAM+ exosomes of NSCLC patients in relation to healthy controls (p=0.0001, CV=11.2%). (B) Parallel ELISA analysis confirmed the overexpression of IGF-1R in total exosomes purified from the same subjects by ultracentrifugation (p=0.0097, CV=56.4%). The error bars are standard deviations (n=3) in all cases.
Figure 5:
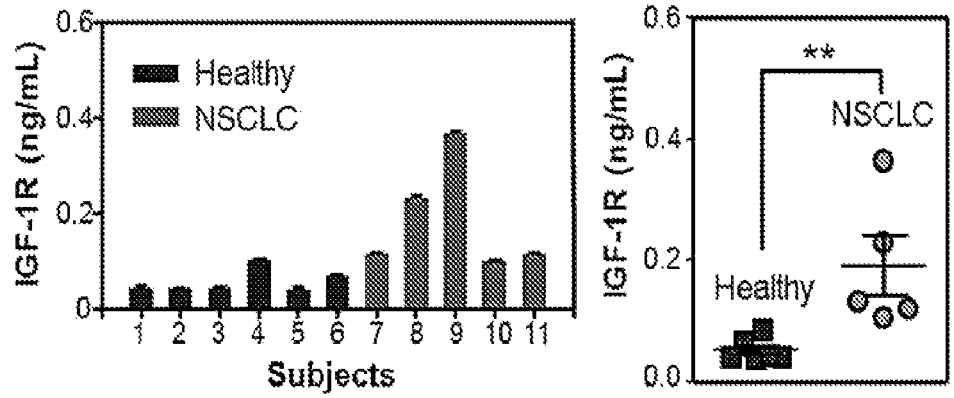
Figure 13:
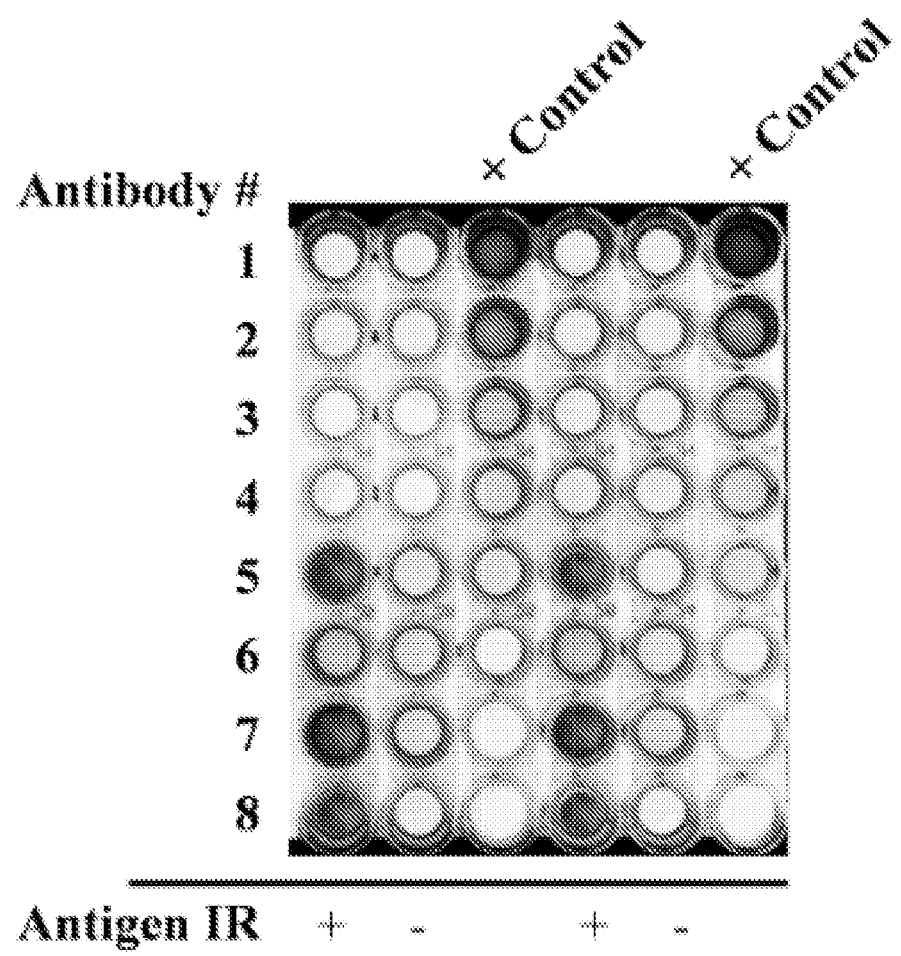
FIG. 13. Photograph of experiment testing cross-reactivity test of IGF-1R antibodies to IR protein using microplate ELISA. No cross-reactivity was observed between total IGF-1R antibodies and IR. In comparison, cross-reactivity of anti-p-IGF-1R with IR was detected. The antibodies against total IGF-1R (#1-4) and p-IGF-1R (#5-8) were obtained from different vendors, as listed in Table 1.
Figure 15:
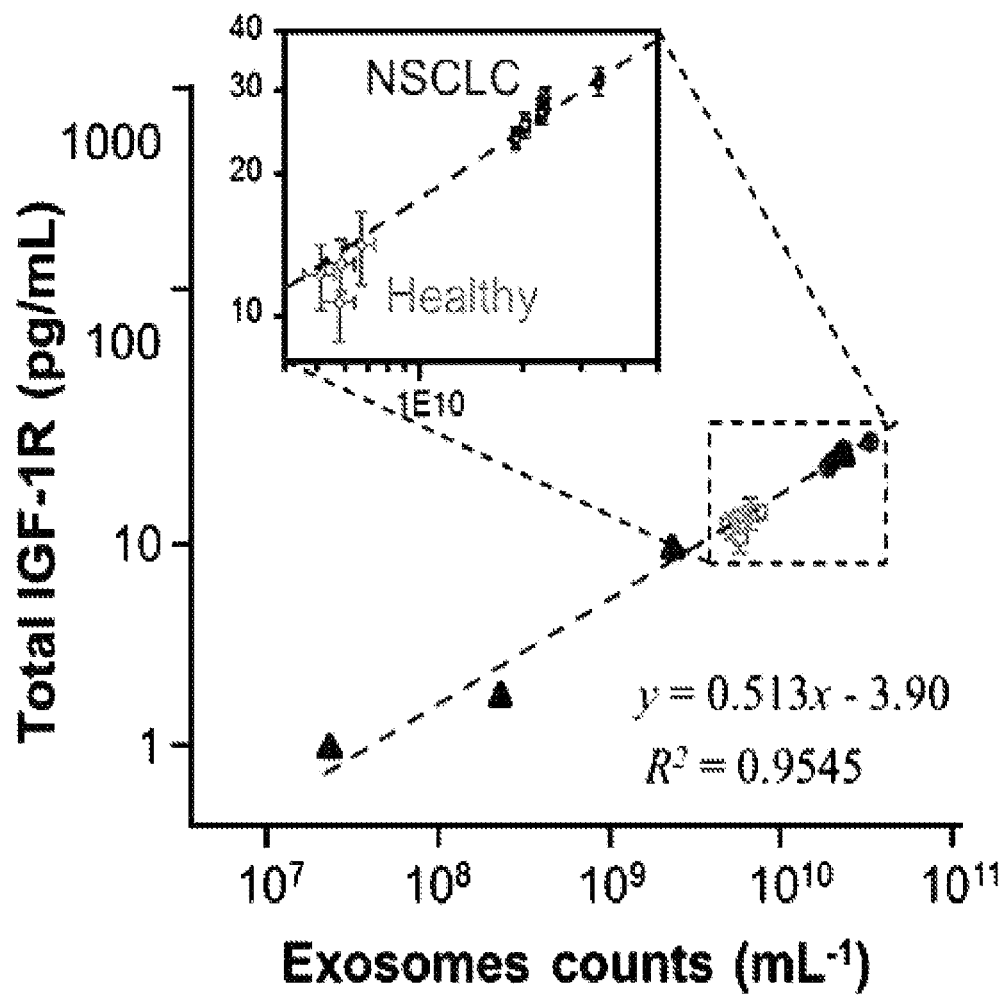

We implemented the integrated microfluidic analysis to examine membrane protein IGF-1R and intravesicular p-IGF-1R directly in the plasma of early-stage NSCLC patients (stage II). The microfluidic results were compared to parallel ELISA analysis of ultracentrifugation-purified vesicles from the same patients (2 mL plasma). To avoid the interference from plasma IGF-1R, we used an EpCAM antibody to capture tumor-derived exosome subpopulations in 30 μL patient plasma. A potential problem may arise from the cross-reactivity of the antibodies with insulin receptor (IR) which shares 80% homology with IGF-1R. To investigate this effect, we tested IGF-1R and p-IGF-1R antibodies from a number of vendors using a commercial IR ELISA kit (Table 1). No cross-reaction with IR was detected for all the IGF-1R antibodies (FIG. 13). FIG. 5A shows that the NSCLC patients overexpress circulating exosomes with an EpCAM+/IGF-1R+ phenotype and can be well discriminated from the control group (p<0.0001). The detected IGF-1R concentration was found to correlate linearly with the total abundance of plasma vesicles determined by NTA, while our method measured a fraction of the circulating vesicles (FIG. 15). In addition, the quantitative detection was achieved for vesicle concentrations much lower than the healthy levels. These results validate the method for sensitive and quantitative characterization of circulating exosomes in clinical samples. IGF-1R overexpression was also evident in the ELISA results presented in FIG. 5B (p<0.01), consistent with the previous observations reported for NSCLC cell lines and tumor tissues. It is notable that ELISA detects the total IGF-1R level in all vesicle types co-purified by ultracentrifugation, while our method enables characterization of molecularly defined subpopulations.

Figure 16:
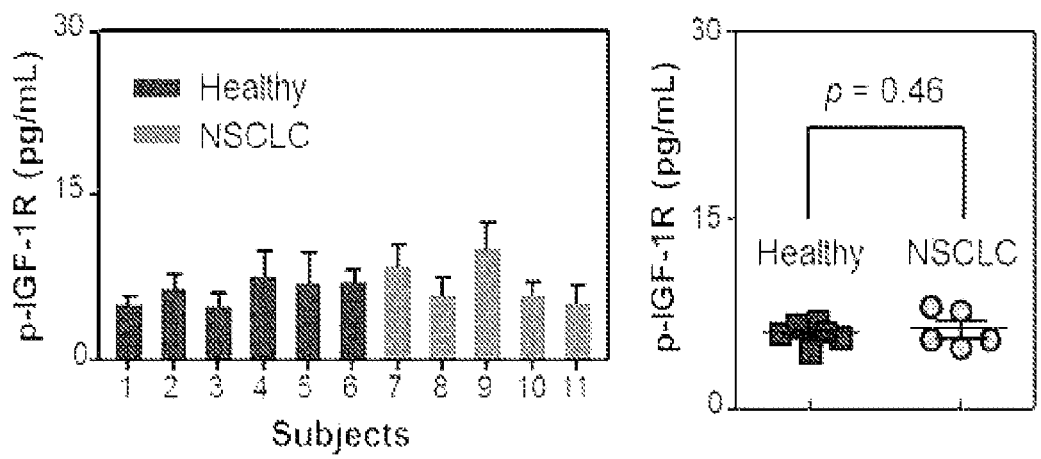
FIG. 16. Graphs showing quantitative analysis of intravesicular p-IGF-1R in circulating exosomes using the same clinical samples as in FIG. 5. (A) Bar (left) and scattered dot (right) plots of the microfluidic results shows no significant difference of the p-IGF-1R level in the EpCAM+ exosomes between NSCLC and healthy subjects (p=0.46). (B) No correlation between the p-IGF-1R level and the disease state was verified by ELISA analysis (p=0.31). The error bars are standard deviations (n=3) in all cases.
Figure 16:
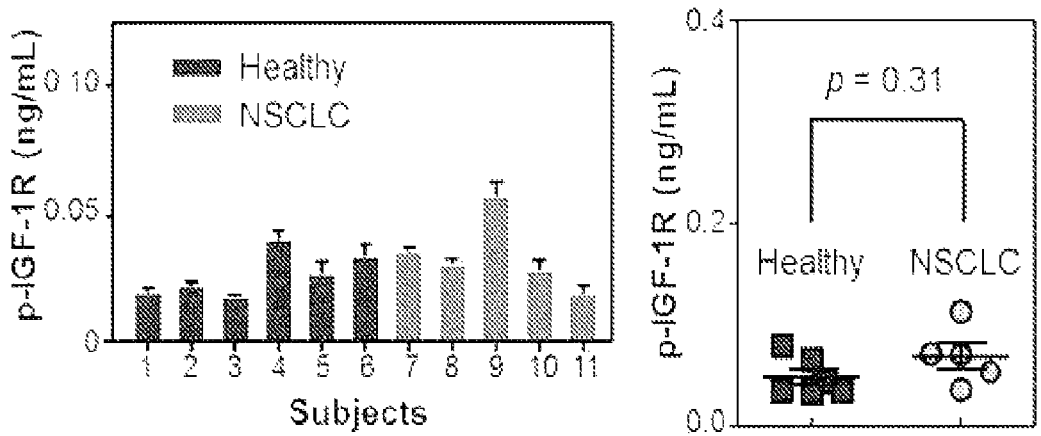

The ability to probe intravesicular contents of selected subpopulations is critical for comprehensive characterization of exosomes and elucidation of their biological and pathological implications. To this end, we measured the intravesicular level of phosphorylated IGF-1R using the same samples as above. Although considerable cross-talking was observed between p-IGF-1R antibodies and IR, (FIG. 13), our method is able to specifically detect p-IGF-1R without IR interference because exosomal p-IGF-1R is captured by the monoclonal anti-IGF-1R beads, followed by washing to remove other exosomal species. As seen in FIG. 16A, the p-IGF-1R profile showed no correlation with that of IGF-1R and the disease state, which was further confirmed by the ELISA analysis (FIG. 16B). This result confirms the specificity of the antibodies for detection of p-IGF-1R without discernable cross-reaction with IGF-1R.

It will be recognized from the foregoing that the present disclosure demonstrates microfluidic isolation and targeted proteomic analysis of exosomes directly from clinical plasma samples, all integrated in one rapid workflow with high sensitivity and specificity. Since many specific antibodies for cancer biomarkers are commercially available, the present method can be readily extended for multiplexed proteomic analysis of circulating exosomes in various cancer types. The plasma volume required to demonstrate the unique features of the present approach was only ~1/100 of that for the conventional protocols, indicating highly efficient exosome immunocapture and sensitive protein analysis of our method. This advantage immediately addresses the challenges in exosomes, purification, which has been until now a key setback in clinical development of exosomal biomarkers.

Example 5

This Example provides a description of the materials and methods used to produce the results described above.

Reagents, chemicals, and antibodies. The stock solution of 10% Triton X-100 was purchased from Roche Diagnostics for making exosome lysis buffer. The fluorogenic substrate DiFMUP (6,8-difluoro-4-methylumbelliferyl phosphate) was purchased from Invitrogen, stored in DMSO solution in dark in a −20° C. freezer, and freshly prepared before each use. The recombinant standard human IGF-1R and phosphorylated IGF-1R proteins were purchased from R&D system. The antibodies used in the study have been listed in Table 1. The crossreactivity of antibodies from different vendors against α-IGF-1R and phospho-IGF-1R has been tested using a ELISA kit (Insulin Receptor β-subunit KHR9111, Invitrogen) to ensure the antibody specificity to IGF-1R.

| No. | Target/human | Vendor | Catalog No | Clone |
|---|---|---|---|---|
| 1 | IGF-1R-biotin | Bioss | bs-0227R-Biotin/poly rabbit | |
| 2 | Total IGF-1R-biotin | R & D | DYC305-2/poly rabbit | |
| 3 | IGF-1R β | Cell signaling | #3027/poly rabbit | |
| 4 | IGF-1R | R&D | MAB391/mono mouse | 33255 |
| 5 | IGF-1R (pTyr1165/1166) | Enogene | E011088-1/poly rabbit | |
| 6 | IGF-1R (pTyr1161) | Acris | AP01610PU-N/poly rabbit | |
| 7 | IGF-1R(pTyr1161/1165/1166) | Millipore | ABE332/poly rabbit | |
| 8 | IGF-1R (pTyr1131) | Cell signaling | #3021/poly rabbit | |
| | IGF-1R α, Biotin | Thermal Scientific | MA5-13799/mono mouse | 24-31 |
| | EpCAM, Biotin | abcam | ab79079/mono mouse | VU-1D9 |
| | CD9, Biotin | abcam | ab28094/mono mouse | MEM-61 |
| | CD63, Biotin | Ancell | 215-030/mono mouse | AHN16.1/46-4-5 |
| | CD81, Biotin | Ancell | 302-030/mono mouse | 1.3.3.22 |
| | CA125, Biotin | MyBioSource | MBS531893/mono mouse | X52 |
| | CA125, Biotin | Fitzgerald | 61R-C112bBT/mono mouse | X52 |
| | Anti-rabbit IgG-AP | A&B | T2191 | |

Microfabrication. The microfluidic exosome profiling device was composed of a poly(dimethylsiloxane) (PDMS) layer sealed with a glass slide. The PDMS device was fabricated using the standard soft lithography. A master was made by patterning SUS photoresist on a 4-inch silicon wafer and was silanized to facilitate removal of PDMS. Negative PDMS replicas were made by pouring a 10:1 mixture of PDMS base with the curing agent over the wafer, followed by curing at 60° C. overnight. After removing the replicas from the master, the fluidic interfacing holes were punched at desired location. The PDMS layer was bonded to a clean glass substrate to form the enclosed microchannels immediately after exposing to UV Ozone for 3 min. The deactivation of PDMS microfluidic channel was conducted using (3-aminopropyl) trimethoxy silane treatment. Briefly, the PDMS microfluidic channel was continuously flushed with a mixture of H2O/H2O2/HCl (volume ratio of 5:1:1) for 30 min to obtain the hydrophilic silanol-covered surface. After purging the microchannel with deionized water and dry Ar, the neat (3-aminopropyl) trimethoxy silane (Sigma-Aldrich) was pumped into the microchannel at room temperature for 10 min. The unreacted silane was flushed out using deionized water mixed with ethanol (1:1) to generate hydrophilic surface. The non-specific binding was further minimized by employing the blocking buffer (1% BSA containing 0.1% Tween 20) and washing buffer (1×PBS buffer, 0.01% Tween 20).

Microfluidic exosome analysis protocol. The detailed protocol for on-chip exosome assay is illustrated in Table 2 and FIG. 1. Reagent delivery was precisely controlled using a 4-syringe programmable pump system (HARVARD Pump 11 Elite). Plasma samples (30-150 μL) pre-mixed with immunomagnetic microbeads were introduced through the inlet 1 into the first-stage magnetic capture chamber at a flow rate of 2 μL/min for the immunomagnetic isolation of exosomes (Step 1). A lysis buffer was then flowed into the first-stage magnetic chamber and stopped for incubation with the beads to completely lyse the exosomes (Step 2). The lysate in the first-stage magnetic capture chamber was subsequently flowed into the serpentine mixing microchannels for immunomagnetic capture of released exosomal protein markers (Step 3). Protein capture microbeads were then collected at the second-stage magnetic chamber for sandwich immunodetection using the diluted primary detection antibodies (1:100) (inlet 3, Step 4). The secondary antibody anti-rabbit IgG-AP (1:100 dilution) was introduced (inlet 3, Step 5), followed by the introduction of the fluorogenic substrate DiFMUP for quantitative and sensitive chemifluorescence detection (inlet 4, Step 6).

TABLE 2

Workflow of microfluidic exosome profiling.

| | Step 1 | Step 2 | Step 3 | Step 4 | Step 5 | Step 6 |
|---|---|---|---|---|---|---|
| | Inlet 1 Plasma sample Inlet 2,3,4 1 × PBS, 0.01% TW20 | Inlet 2 5% Triton X-100 Inlet 1,3,4 1 × PBS, 0.01% TW20 Stop flow for 10 min | Inlet 3 anti-total IGF-1R magnetic beads Inlet 1,2,4 1 × PBS, 0.01% TW20 | Inlet 3 anti total IGF-1R (1:100) Inlet 1,2,4 1 × PBS, 0.01% TW20 | Inlet 3 anti-rabbit IgG-AP (1:100) Inlet 1,2,4 1 × PBS, 0.01% TW20 | Inlet 4 1 mM DiFMUP solution Inlet 1,2,3 1 × PBS, 0.01% TW20 Incubate for 6 min |
| Flow rate | 2 uL/min | 1 μL/min | 1 μL/min | 1 μL/min | 1 μL/min | 1 μL/min |
| Duration | 15 min | 5 min | 30 min | 10 min | 10 min | 5 min |

The washing buffer has been optimized to minimize bead aggregation and non-specific adsorption while maintaining the integrity of captured exosomes. Tween 20 is a commonly used non-ionic surfactant for immunoassays and has been reported as a buffer addictive at low concentrations (0.05%)

for exosome processing and analysis 1. We have tested 1×PBS buffer with Tween 20 at different concentrations (0, 0.01%, 0.1%, 1%) and observed that 0.01% tween 20 can effectively remove non-specific adsorption (FIG. 2) and prevent the formation of bead aggregation and protein/vesicle clumps which otherwise were often observed during magnetic capture without Tween 20 added. Through TEM examination, it was observed that the captured exosomes remain intact. The washing buffer (1×PBS, 0.01% Tween 20) was employed for 5 min between each step. To maximize the recovery of released exosomal proteins, a total volume of 30 µL buffer was continuously infused to wash the exosome-binding beads captured in the first chamber and then mixed with the protein-binding beads, which were finally collected in the second chamber for downstream protein assays (Table 1). The washing buffer has been optimized to minimize bead aggregation and non-specific adsorption while maintaining the integrity of captured exosomes. Tween 20 is a commonly used non-ionic surfactant for immunoassays and has been reported as a buffer addictive at low concentrations (0.05%) for exosome processing and analysis[1]. We have tested 1×PBS buffer with Tween 20 at different concentrations (0, 0.01%, 0.1%, 1%) and observed that 0.01% tween 20 can effectively remove non-specific adsorption (FIG. 2) and prevent the formation of bead aggregation and protein/vesicle clumps which otherwise were often observed during magnetic capture without Tween 20 added. Through TEM examination, it was observed that the captured exosomes remain intact. The washing buffer (1×PBS, 0.01% Tween 20) was employed for 5 min between each step. To maximize the recovery of released exosomal proteins, a total volume of 30 µL buffer was continuously infused to wash the exosome-binding beads captured in the first chamber and then mixed with the protein-binding beads, which were finally collected in the second chamber for downstream protein assays (Table 1).

Figure 17:
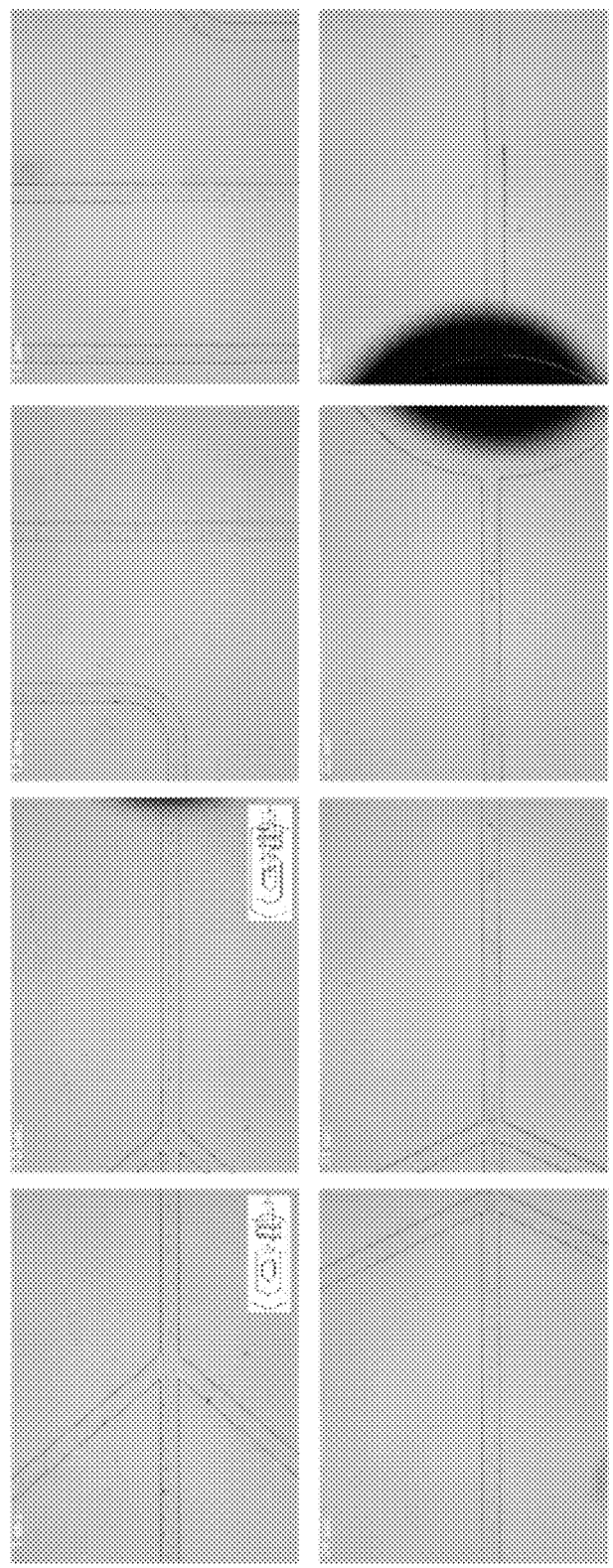
FIG. 17. Screen capture of movie showing device architecture and workflow of microfluidic immunomagnetic beads manipulation for exosome profiling. The microscope stage was moved to observe in the order of injection channel, the first-stage magnetic capture chamber, serpentine mixing microchannel, and the second magnetic capture chamber. The two cascading magnetic-bead capture chambers are of 4-mm diameter and are capable of capturing up to 109 2.8 µm microbeads each. The length of the serpentine channel is 25 cm.

FIG. 17 shows a screen capture from a movie of the device architecture and workflow of microfluidic immunomagnetic beads manipulation for exosome profiling. The field of view was highlighted in the sequence images. The microscope stage was moved to observe in the order of injection channel, the first-stage magnetic capture chamber, serpentine mixing microchannel, and the second magnetic capture chamber. The two cascading magnetic-bead capture chambers are of 4-mm diameter and are capable of capturing up to $10^9$ 2.8 µm microbeads each. The length of the serpentine channel is 25 mm.

Immunomagnetic beads and antibody coupling. Streptavidin-coated magnetic microbeads (Dynal beads M-270, 2.8 µm in diameter) were purchased from Invitrogen. Antibodies against α-IGF-1R, EpCAM, CD9, CD81, and CD63 (Table 1) were coupled to the Dynal beads through biotin-streptavidin linkage per the instruction, generating typical binding capacity of ~10 µg biotinylated antibody per 1 mg of beads. We pre-mixed 20 µL of antibody-coated beads (1 mg/mL) with 30-150 µL human plasma for 30 min, and then introduced the mixture into the microfluidic device. A disk magnet (Licensed NdFeB, Grade N40, 2-mm in diameter, poles on flat face) was used to retained the magnetic beads. The IGF-1R capture beads were generated by coupling mouse monoclonal IGF-1R antibody (R&D, MAB391) to surface-activated Dynabeads (M-270 Epoxy, 2.8 µm in diameter) through epoxy-amine covalent bonds. The epoxy coupling reaction was performed at 37'C overnight with gentle shaking, following the manufacture's instruction. The typical binding capacity is ~5-8 µg antibody per 1 mg of beads.

Patient plasma and tissue samples. Human blood samples and tumor tissues were collected from healthy donors, NSCLC and ovarian cancer patients. De-identified samples were obtained from the University of Kansas Cancer Center's Biospecimen Repository Core Facility after approval from the internal Human Subjects Committee. Table 3 provides a list of human samples used in this disclosure.

TABLE 3

| Patient ID | Age | Sex | Smoking history | Cancer stage* | Treatment | Sample |
|---|---|---|---|---|---|---|
| 1385 | 62 | F | Yes | NSCLC PT2PN1MX | N | Plasma Lower lobe lung tumor |
| 1357 | 40 | F | No | NSCLC PT2PN0MX | N | Plasma Lower lobe lung tumor |
| 1076 | 60 | F | Yes | NSCLC PT2PN1MX | Y | Plasma Lower lobe lung tumor |
| 1187 | 48 | F | Yes | NSCLC PT2PN0MX | N | Plasma |
| 6467 | 73 | F | Yes | NSCLC PT2PN0MX | N | Plasma |
| 4699 | 62 | F | Yes | NSCLC PT2PN1MX | N | Plasma |
| 3505 | 73 | F | Yes | NSCLC PT2PN0MX | N | Plasma |
| 4311 | 52 | F | No | Healthy | — | Pia:stria |
| 4308 | 52 | F | No | Healthy | — | Plasma |
| 4309 | 76 | F | No | Healthy | — | Plasma |
| 4310 | 40 | F | No | Heal thy | — | Plasma |
| 4272 | 52 | F | No | Healthy | — | Plasma |
| 4276 | 42 | F | No | Healthy | — | Plasma |
| 4266 | 63 | F | No | Healthy | — | Plasma |

De-identified samples and matching information were obtained from University of Kansas Cancer Center's Biospecimen Repository.
*using TNM (Tumor, Node, Metastasis) pathologic staging system.

Differential Ultracentrifugation and Bradford Assay.

The exosome-like microvesicles were prepared from frozen blood plasma (2 mL) or cell culture media. The plasma was first centrifuged at 10,800 rpm for 45 min at 4° C. using an ultracentrifuge (Thermo Scientific SORVALL WX ULTRA series centrifuge). Supernatants were then purified by two successive centrifugations for 2 hours, each at 35,800 rpm. Pellets were washed once by ultracentrifugation in 20 µL PBS, and resuspended in 20 µL PBS. The amount of pellets recovered was measured by Bradford assay (Bio-Rad). The Bradford reagent concentrate was diluted at 1:5 ratio and mixed with 10 µL of ultracentrifugation-collected pellets. BSA standards were used to calibrate total exosome protein contents. A UV spectrometer (Beckman DU640) was used to measure the UV absorbance at 595 nm of samples in disposable cuvettes for three times. The purified microvesicles were conserved at −80° C. until use.

Nanoparticle tracking analysis (NTA). Ultracentrifugation-purified vesicles were diluted in 1:50, 1:125, 1:250, and 1:500 in 1×PBS buffer in molecular grade water. NanoSight LM10 with a monochromatic 404 nm (blue) laser (NanoSight) was used to perform size analysis of 300 µL of exosome samples. Video files of 30-60 s duration with a frame rate of 25 frame per second were recorded and analyzed using the Nanoparticle Tracking Analysis software version 2.3. By monitoring the trajectory of microvesicle movement, particle number and size distribution within the range of 0-500 nm were estimated. For consistent reading, the measurement settings were optimized and five replicas were performed to obtain the averaged measurements.

Transmission electron microscopy and image analysis. Compared to nanoparticle tracking analysis (NTA) by NanoSight which requires ~1 mL of concentrated vesicles (~109 mL-1) for accurate size determination, TEM provides a robust means for sizing and counting of exosomes in small-volumes collected from microfluidic isolation without significant dilution (~30 μL). A two-step embedding protocol using agar and resin was developed to ensure that exosome morphology was maximally maintained under TEM imaging. The exosome-bead complexes were fixed in 2% (v/v) glutaraldehyde in PBS for 1 h, followed by two 15-min washes in PBS. Beads were re-suspended in 4% agar. After cutting the agar into 1-mm pieces, the specimen was fixed overnight in 2% (w/v) osmium tetroxide in 0.1 M cacodylate buffer kept in refrigerator. The specimen was rinsed 2 times with distilled water for 15 min each. Then the specimen was dehydrated in a graded series of ethanol: 30% for 10 min, 70% for 10 min, 95% for 10 min, 100% for 30 min, 100% for 30 min. Then the specimen was placed into a graded series of mix of pure L.R. white (hard grade) and 100% ethanol: 1:2 for 30 min, 1:1 for 30 min, 2:1 for 30 min. Then three changes of ethanol-free pure L.R. white were conducted for 30 min, and kept overnight. The resin embedded specimen was polymerized at 60° C. for 24 h. Ultra-thin sections (80 nm) were cut on Leica Ultracut-S Ultramicrotome, and counterstained with 4% (w/v) aqueous uranyl acetate for 5 min, followed by 3 min with a solution of lead acetate. The stained sections were viewed in a JEOL JEM-1400 Transmission Electron Microscope (equipped with a Lab6 gun) operated at 80 kV. Micrographs were acquired at a known scale. The size of vesicles bound to the bead surface was measured using JEM-1400 TEM software with ruler function at 20 K magnification and normalized to the scale bar.

For TEM imaging of ultracentrifugation-purified exosomes without two-step embedding, a drop of purified exosome sample, approximately 10 μg of the intact exosomes, was placed on a parafilm. A formvar carbon coated nickel grid on top of each drop was positioned gently on top of each drop for 30 minutes. The coating side is faced to the drop containing exosomes. Then the grid was washed by sequentially positioning on top of PBS drops for three times. The prepared sample was fixed by putting the grid on a drop of 2% paraformaldehyde, counterstained in 2% uranyl acetate for 15 minutes, embedded using 0.13% methyl cellulose and 0.4% uranyl acetate for 10-minute incubation, and then imaged by TEM.

Western blot analysis. Western blotting was performed using 4-12% precast polyacrylamide slab mini-gels (Tris-glycine pH 8.3) with Blot Module (BioRad), following the standard protocol. Exosome samples were lysed by adding running buffer (0.1% SDS) and heating at 65° C. for 5 min. After electrophoresis at 125 V for 2 h, gels were electrotransferred to cellulose membranes (0.2 μm) at 25 V for 2.5 h. After twice washing (1×PBS, 0.5% Tween 20, pH 7.4), the membranes were blocked with 5% dry milk overnight at 4° C. with shaking. The solution of primary antibody (1:1000) was added into blocking buffer for 2-h incubation with shaking at room temperature. After incubation, the membranes were washed 3 times for 10 min each. The secondary antibody streptavidin-HRP (Invitrogen, ELISA grade, 1.1 mg/mL) diluted 1:2500 in the blocking solution was added for 1-h incubation at room temperature with agitation. After that, the washing step was repeated three times. The membrane was subsequently developed with Chromogenic Substrate Reagent (BioRad) until the desired band intensity was achieved. Imaging was performed by using FluorChem E (ProteinSimple) with a appropriate filter.

Three-color Immunofluorescence histology (IFH) analysis. The three-color immunofluorescence staining was performed following the standard protocol. The fresh frozen lung tumor tissues were embedded in OCT compound in cryomolds and cut into 4 μm thick cryostat sections, and mounted on superfrost plus slides. Before staining, slides were placed at room temperature for 30 min, and fixed in ice cold acetone for 5 min. After 30-min air dry, slides were rinsed with PBS-T buffer for 2 min and repeated once. 1% bovine serum albumin was used to block the tissue sections for 30 min. Lung tumor tissues exhibit strong natural biotin, thus the tissue sections were blocked with avidin and biotin solution sequentially (SP-2001, Vector Laboratories Inc) for 15 min each, and rinsed twice in PBS-T buffer for 2 min each. The primary antibodies (biotinylated mouse monoclonal anti α-IGF-1R, EpCAM, CD9, CD81, CD63) were added at 1:100 dilution. The negative control was the omission of primary antibody. The incubation was conducted overnight at 4° C. After washing with PBS-T, 0.4 μM DAPI (sc-3598, Santa Cruz Biotechnology) in PBS, avidin-FITC (1:3000, MBS538905, MyBioSource), and positive control antibody CDK2 (1:50, sc-748 Santa Cruz Biotechnology) were incubated sequentially with the tissue sections. The secondary detection antibody goat anti-rabbit IgG (F(ab')2-PE-Cy5 (1:100, sc-3844, Santa Cruz Biotechnology) was incubated with sections for 1 hour after washing. After staining, the sections were mounted by coverslips with flourogold G mounting media (0100-01, SouthernBiotech). The stained tissue sections were imaged using an upright epi-fluorescence microscope (Nikon Eclipse 80i) equipped with the CCD camera (oneCLICK, QImaging), 40× objective (N.A.=0.75), and three color filter sets (blue, green, red). The exposure time was 1000 ms. Images were collected and merged in three-color using Metamorph. Three replicas were performed for each subjects. The fluorescence intensity was measured and normalized to the negative control using ImageJ.

Protein chemifluorescence detection. According to the Michaelis-Menten equation, at the maximum concentration of substrate (saturation), the turn-over rate of an enzymatic reaction is fastest and independent of the substrate concentration. Under the enzyme-limiting conditions, the turn-over rate rises linearly with the increase of enzyme concentration, which is reflected by converting more DiFMUP substrate to strongly fluorescent DiFMU product. Thus, by applying saturating DiFMUP concentration, a linear relationship between the rates of product conversion and the amount of enzyme presented in the second-stage magnetic chamber can be obtained. To obtain a saturating substrate concentration in the reaction chamber, a 1000 μM DiFMUP solution diluted from 10 mM stock solution of DiFMUP in DMSO was introduced for 5 min and then stopped for enzymatic reaction. Accumulation of fluorescent DiFMU during the assay occurred linearly and then reached a maximum as the equilibrium is achieved (FIG. 4E). The incubation time is an important factor for the detection in our system because the second capture chamber is not completely closed after the flow is stopped. We found that the fluorescent signal reaches maximum after 6 min incubation, which may be attributed to the balance between the enzymatic conversion and the diffusion of the fluorescent product out of the chamber. An incubation time of 6 min was applied consistently throughout all measurements. Calibration curves were generated for IGF-1R and p-IGF-1R to correlate the fluorescence signals with given protein concentrations.

Data Acquisition and Analysis. Image and video capture was performed by an upright epifluorescence microscope (Nikon Eclipse 80i) equipped with a mechanical shutter and a CCD camera (oneCLICK, QImaging) using a 4× (N.A.=0.1) or 10× objective (N.A.=0.3). The camera exposure time was set to 500 ms with a 10 MHz frequency controlled by Metamorph. A filter set (excitation 325-375 nm, emission 435-485) was used for UV illumination by a Xenon Lamp and for fluorescence detection. Image analysis was performed using ImageJ and consistent regions of interest were defined and analysed. The measured fluorescent signal was corrected for the background signal.

Standard ELISA measurement of IGF-1R and p-IGF-1R in ultracentrifugation-purified plasma exosomes. Following the protocols provided by the manufacturers, commercial ELISA kits for human IGF-1R (OK-0226, OmniKine) and IGF-1R[pYpY1135/1136] (KHO0501, Invitrogen) were used to measure the concentration of endogenous IGF-1R and pIGF-1R in human plasma derived exosomes, respectively. The plasma samples from Stage II NSCLC patients employed here match with those for the on-chip measurements. The ultracentrifugation purified exosomes were lysed by 5% Triton X-100, consistent with the on-chip lysis protocol. Then the lysates were diluted by 10 or 100 folds to prepare 100 µL standards which were then loaded into 96-well plate pre-coated with the antibody against α-IGF-1R. Each concentration was measured three times to obtain the average signal. Absorbance was read out in each well at 450 nm using a TECAN plate reader (infinite V200 pro). The background absorbance was substracted from all data points. The standard calibration curves were established by plotting the absorbance of the standard IGF-1R and pIGF-1R proteins against the standard concentrations. The concentrations for total IGF-1R and p-IGF-1R from human plasma samples were determined using the standard calibration curves.

Test of crossreactivity of IGF-1R antibodies with insulin receptor (IR). IGF-1R has over 80% homology with insulin receptor (IR) by sharing the conserved tyrosine residues that are phosphorylated 2. This homology makes it difficult to differentiate the phosphorylation from total IGF-1R with IR expression level, due to the crossreactivity of many commercial phospho-IGF-1R antibodies with phosphorylated IR3-6. In our approach, p-IGF-1R molecules released from exosomes are captured by the beads coated with the antibody specific for total IGF-1R and washed to remove interfering IR protein if present. Thus it is important to ensure the specificity of the IGF-1R antibody. To this end, the crossreactivity of IGF-1R antibodies from various vendors with IR was evaluated using an Insulin Receptor β ELISA kit (KHR9111, Invitrogen) (FIG. 13). The antibodies tested here were listed in Table 1. The monoclonal antibody specific for IR (regardless of phosphorylation state) was pre-coated onto the wells of the microtiter strips. The strips 1, 2 and 3 are the replicas of strips 4, 5 and 6 (left to right). The IR antigen standard (15 ng/mL) was added to strips 1 and 4, but not in strips 2 and 5. Serial dilutions of IR (30, 15, 7.5, 3.75, 1.87, 0.94, and 0 ng/mL) were added to strip 3 and 6 as positive controls. After incubation and washing, the various IGF-1R antibodies (Table 1) were added to strip 1, 2, 4 and 5, in the order indicated in the FIG. 13 and Table 1. The antibody specific for IR was added to strip 3 and 6 for detection of standard IR as parallel control. After a second incubation and washing, horseradish peroxidase-labeled anti rabbit IgG was added and bound to the detection antibody (anti-mouse IgG HRP was used for antibody #4). Following the third incubation and washing, the substrate solution was added and the absorbance was read using a TECAN plate reader. As shown in FIG. 13, the antibodies to total IGF-1R did not crossreact with IR. As expected, the p-IGF-1R antibodies from four different vendors showed considerable crossreactivity to IR. Thus, we selected the antibody against total IGF-1R for capture, which avoids non-specific interference and improves the specificity for p-IGF-1R detection.

While the disclosure has been particularly shown and described with reference to specific embodiments (some of which are preferred embodiments), it should be understood by those having skill in the art that various changes in form and detail may be made therein without departing from the scope of the present disclosure as disclosed herein. Hence, the present invention is deemed limited only by the appended claims and the reasonable interpretation thereof.

What is claimed is:

1. A method of diagnosis, or for aiding in diagnosis, or for monitoring treatment of a subject comprising processing a sample obtained or derived from the subject with a microfluidic chip comprising:
    a first capture chamber configured to enable immunomagnetic isolation;
    a second capture chamber configured to enable protein analysis;
    a serpentine microchannel connecting the first capture chamber and the second capture chamber;
    a first microchannel connecting the first capture chamber and the serpentine microchannel;
    a second microchannel connecting the serpentine microchannel and the second capture chamber;
    a sample inlet connected to the first capture chamber;
    a buffer inlet connected to the first capture chamber;
    a bead inlet;
    at least a first connector channel connected to the bead inlet and the first microchannel, wherein the first connector channel is connected to the first microchannel upstream of the serpentine microchannel and downstream of the first capture chamber; and
    a reagent inlet connected to the second microchannel upstream of the second capture chamber and downstream of the serpentine microchannel,
    wherein the method comprises detecting a signal from a detectably labeled antibody, wherein the antibody is specifically bound to a protein marker that was present in exosomes in the sample obtained or derived from the subject, wherein the presence of the protein marker is positively correlated with a condition that the subject is at risk for developing, is suspected of having, or has been diagnosed with, wherein the signal from the detectably labeled antibody is generated in the second capture chamber, wherein the processing the sample comprises introducing the sample into the sample inlet, introducing antibodies specific for an exosome surface marker into the reagent inlet, wherein the antibodies are conjugated to magnetic beads, adding a buffer comprising 0.01% Tween 20 into the buffer inlet such that the buffer contacts the sample, capturing exosomes in the first capture chamber, lysing the exosomes such that that the surface proteins are released and are mixed with antibodies in the serpentine microchannel, magnetically capturing complexes comprising the antibodies and the exosome surface proteins in the second capture chamber, and detecting a signal from the antibodies to quantify the surface proteins, wherein the time from introducing the sample into the sample outlet to formation of the complexes comprising the antibodies so that the signal from the antibodies can be detected is less than 1.5 hours.

2. The method of claim 1, wherein the first capture chamber and the second capture chamber are approximately 4 mm in diameter and are configured to each capture up to approximately $10^9$ 2.8 mm microbeads.

3. The method of claim 1, wherein the first capture chamber is configured to isolate magnetic microbeads with bound exosomes from a fluid sample.

4. The method of claim 1, further comprising a second connector channel connected to the bead inlet and the first microchannel, wherein the second connector channel is connected to the first microchannel upstream of the serpentine microchannel and downstream of the first capture chamber.

5. The method of claim 1, wherein the first connector channel has dimensions configured to enable magnetic microbeads to pass there through.

6. The method of claim 1, further comprising at least one syringe pump connected to one of the sample inlet, the buffer inlet, the bead inlet, or the reagent inlet, wherein the syringe pump is configured to have picoliter resolution.

7. The method of claim 1, further comprising a magnet positioned opposite of a surface of the microfluidic chip.

8. The method of claim 1, wherein the microfluidic chip is fabricated of a glass substrate and a layer of poly(dimethylsiloxane).

9. The method of claim 1, wherein the serpentine microchannel has at least one surface that is hydrophilic.

10. The method of claim 1, further comprising an outlet connected to the second capture chamber.

11. The method of claim 1, further comprising a four syringe pump connected to the sample inlet, the buffer inlet, the bead inlet, and the reagent inlet.

12. The method of claim 1, wherein the sample comprises plasma.

13. The method of claim 1, wherein the protein marker is a cancer marker.

* * * * *